United States Patent
Turtle et al.

(10) Patent No.: US 10,653,756 B2
(45) Date of Patent: *May 19, 2020

(54) IDENTIFICATION OF CD8+ T CELLS THAT ARE CD161$^{hi}$ AND/OR IL18R($\alpha$)$^{hi}$ AND HAVE RAPID DRUG EFFLUX CAPACITY

(71) Applicant: FRED HUTCHINSON CANCER RESEARCH CENTER, Seattle, WA (US)

(72) Inventors: Cameron J. Turtle, Seattle, WA (US); Stanley R. Riddell, Sammamish, WA (US)

(73) Assignee: Fred Hutchinson Cancer Research Center, Seattle, WA (US)

(*) Notice: Subject to any disclaimer, the term of this patent is extended or adjusted under 35 U.S.C. 154(b) by 157 days.

This patent is subject to a terminal disclaimer.

(21) Appl. No.: 15/903,214

(22) Filed: Feb. 23, 2018

(65) Prior Publication Data

US 2018/0243386 A1 Aug. 30, 2018

Related U.S. Application Data

(60) Continuation of application No. 14/810,286, filed on Jul. 27, 2015, now Pat. No. 9,931,384, which is a division of application No. 12/865,221, filed as application No. PCT/US2009/000554 on Jan. 28, 2009, now Pat. No. 9,090,875.

(60) Provisional application No. 61/024,241, filed on Jan. 29, 2008.

(51) Int. Cl.
*C12N 5/0783* (2010.01)
*A61K 39/00* (2006.01)
*G01N 33/50* (2006.01)
*A61K 35/17* (2015.01)

(52) U.S. Cl.
CPC .............. *A61K 39/00* (2013.01); *A61K 35/17* (2013.01); *C12N 5/0636* (2013.01); *C12N 5/0638* (2013.01); *G01N 33/505* (2013.01); *A61K 2039/515* (2013.01); *A61K 2039/57* (2013.01); *A61K 2039/572* (2013.01); *C12N 2501/599* (2013.01); *G01N 2333/54* (2013.01); *G01N 2333/70557* (2013.01)

(58) Field of Classification Search
None
See application file for complete search history.

(56) References Cited

U.S. PATENT DOCUMENTS

| | | | |
|---|---|---|---|
| 4,474,893 A | 10/1984 | Reading | |
| 4,676,980 A | 6/1987 | Segal et al. | |
| 4,690,915 A | 9/1987 | Rosenberg | |
| 4,816,567 A | 3/1989 | Cabilly et al. | |
| 6,040,177 A | 3/2000 | Riddell et al. | |
| 6,274,118 B1 | 8/2001 | Diamandis et al. | |
| 6,630,576 B2 | 10/2003 | Debinski | |
| 7,279,160 B2 | 10/2007 | Zhou et al. | |
| 9,090,875 B2 * | 7/2015 | Turtle | C12N 5/0636 |
| 2003/0170238 A1 | 9/2003 | Gruenberg et al. | |

FOREIGN PATENT DOCUMENTS

WO 2006/010603 A1 2/2006

OTHER PUBLICATIONS

Becker et al. "Interleukin 15 Is Required for Proliferative Renewal of Virus-specific Memory CD8 T Cells," *J. Exp. Med.* 195(12):1541-1548, 2002.

Beckhove et al. "Specifically activated memory T cell subsets from cancer patients recognize and reject xenotransplanted autologous tumors," *J Clin Invest* 114(1):67-76, 2004.

Berger et al., "Adoptive transfer of effector CD8+ T cells derived from central memory cells establishes persistent T cell memory in primates," *J Clin Invest* 118(1):294-305, 2008.

Billerbeck et al., "Analysis of CD161 expression on human CD8+ T cells defines a distinct functional subset with tissue-homing properties," *PNAS* 107:7:3006-3011, 2010.

Chang et al., "Asymmetric T lymphocyte division in the initiation of adaptive immune responses," *Science* 315:1687-1691, 2007.

Dare et al., "Effect of age on the repertoire of cytotoxic memory (CD8+CD45RO+) T cells in peripheral blood: The use of rearranged T cell receptor γ genes as clonal markers," *Journal of Immunological Methods* 308:1-12, 2006.

Donnenberg et al., "P-glycoprotein (P-gp) is upregulated in peripheral T-cell subsets from solid organ transplant recipients," *J Clin Pharmacol* 41:1271-1279, 2001.

Donnenberg et al., "P-glycoprotein activity is decreased in CD4+ but not CD8++lung allograft—infiltrating T cells during acute cellular rejection," *Transplantation* 77(11):1699-1706, 2004.

Dudley et al., "Adoptive cell transfer therapy following non-myeloablative but lymphodepleting chemotherapy for the treatment of patients with refractory metastatic melanoma," *J Clin Oncol* 23(10):2346-2357, 2005.

Elliott et al., "Multidrug transporter activity in lymphocytes," *Br J Pharmacol* 143:899-907, 2004.

Eshhar, "The T-Body Approach: Redirecting T Cells with Antibody Specificity," in Chernajovsky et al. (eds.), *Therapeutic Antibodies. Handbook of Experimental Pharmacology 181*, Springer-Verlag, Berlin, Germany, 2008, pp. 329-342.

(Continued)

*Primary Examiner* — Zachary S Skelding

(74) *Attorney, Agent, or Firm* — Seed IP Law Group LLP

(57) ABSTRACT

This invention provides, among other things, methods for the identification and isolation of viable putative long-lived antigen-specific memory CD8+ T cell subsets (CMhi and EMhi) with high surface expression of CD161 and/or IL-18Rα and the capacity to rapidly efflux the fluorescent dye Rh123.

15 Claims, 17 Drawing Sheets

Specification includes a Sequence Listing.

(56) References Cited

OTHER PUBLICATIONS

Extended European Search Report dated Aug. 13, 2012, for corresponding EP Application No. 09705748.3, 10 pages.
Fearon et al., "Arrested differentiation, the self-renewing memory lymphocyte, and vaccination," *Science* 293:248-250, 2001.
Ferlini et al., "Rhodamine 123: A Useful Probe for Monitoring T Cell Activation," *Cytometry* 21:284-293, 1995.
Galon et al., "Type, density, and location of immune cells within human colorectal tumors predict clinical outcome," *Science* 313:1960-1964, 2006.
Geginat et al., "Proliferation and differentiation potential of human $CD8^+$ memory T-cell subsets in response to antigen or homeostatic cytokines," *Blood* 101(11):4260-4266, 2003.
Hammarlund et al., "Duration of antiviral immunity after smallpox vaccination," *Nat Med* 9(9):1131-1137, 2003.
Hand et al., "Expression of IL-7 receptor α is necessary but not sufficient for the formation of memory CD8 T cells during viral infection," *Proc Natl Acad Sci USA* 104(28):11730-11735, 2007.
Intlekofer et al., "Effector and memory $CD8^+$ T cell fate coupled by T-bet and eomesodermin," *Nat Immunol* 6(12):1236-1244, 2005.
Itoi et al., "Differential upregulation of interleukin-18 receptor alpha chain between $CD4^+$ and $CD8^+$ T cells during acute graft-versus-host disease in mice," *Journal of Interferon and Cytokine Research* 24:291-296, 2004.
Jabbari et al., "Cutting edge: differential self-peptide/MHC requirement for maintaining CD8 T cell function versus homeostatic proliferation," *J Immunol* 175:4829-4833, 2005.
Kaech et al., "Selective expression of the interleukin 7 receptor identifies effector CD8 T cells that give rise to long-lived memory cells," *Nat Immunol* 4(12):1191-1198, 2003.
Kennedy et al., "Reversible defects in natural killer and memory CD8 T cell lineages in interleukin 15-deficient mice," *J Exp Med* 191(5):771-780, 2000.
Kessler et al., "Identification of T-cell epitopes for cancer immunotherapy," *Leukemia* 21:1859-1874, 2007.
Klebanoff et al., "$CD8^+$ T-cell memory in tumor immunology and immunotherapy," *Immunological Reviews* 211(1):214-224, 2006.
Koebel et al., "Adaptive immunity maintains occult cancer in an equilibrium state," *Nature* 450:903-907, 2007.
Lanzavecchia et al., "Understanding the generation and function of memory T cell subsets," *Curr Opin Immunol* 17:326-332, 2005.
Leen et al., "Improving T Cell Therapy for Cancer," *Annu. Rev. Immunol.* 25:243-265, 2007.
McKenzie et al., "Low rhodamine 123 retention identifies long-term human hematopoietic stem cells within the $Lin^-CD34^+CD38^-$ population," *Blood* 109(2):543-545, 2007.
Memorandum from Deputy Commissioner for Patent Examination Policy Andrew H. Hirshfeld, dated Mar. 4, 2014, 19 pages.
Michalek et al., "Detection and long-term in vivo monitoring of individual tumor-specific T cell clones in patients with metastatic melanoma," *J Immunol* 178:6789-6795, 2007.
Mueller et al., "Increased CD95/Fas-Induced Apoptosis of HIV-Specific $CD8^+$ T Cells," *Immunity* 15:871-882, Dec. 2001.
Murali-Krishna et al., "Persistence of memory CD8 T cells in MHC class I-deficient mice," *Science* 286:1377-1381, 1999.

Pages et al., "Effector memory T cells, early metastasis, and survival in colorectal cancer," *N Engl J Med* 353:2654-2666, 2005.
Prlic et al., "Requirements for CD8 T-cell priming, memory generation and maintenance," *Curr Opin Immunol* 19:315-319, 2007.
Rosenberg et al., "Cancer immunotherapy: moving beyond current vaccines," *Nature Medicine* 10(9):909-915, 2004.
Rezvani et al., "Functional leukemia-associated antigen-specific memory $CD8^+$ T cells exist in healthy individuals and in patients with chronic myelogenous leukemia before and after stem cell transplantation," *Blood* 102(8):2892-2900, 2003.
Robbins et al., "Cutting edge: persistence of transferred lymphocyte clonotypes correlates with cancer regression in patients receiving cell transfer therapy," *J Immunol* 173:7125-7130, 2004.
Sallusto et al., "Central memory and effector memory T cell subsets: function, generation, and maintenance," *Annu Rev Immunol* 22:745-763, 2004.
Sallusto et al., "Two subsets of memory T lymphocytes with distinct homing potentials and effector functions," *Nature* 401:708-712, 1999.
Schinkel et al., "Mammalian drug efflux transporters of the ATP binding cassette (ABC) family: an overview," *Adv Drug Deliv Rev* 55:3-29, 2003.
Schluns et al., "Interleukin-7 mediates the homeostasis of naïve and memory CD8 T cells in vivo," *Nat Immunol* 1(5):426-432, 2000.
Sprent, "T Memory Cells: Quality not Quantity," *Current Biology* 12:R174-R176, 2002.
Takahashi et al., "Expression of CD161 (NKR-P1A) Defines Subsets of Human CD4 and CD8 T Cells with Different Functional Activities," *J Immunol* 176:211-216, 2006.
Tan et al., "Interleukin (IL)-15 and IL-7 jointly regulate homeostatic proliferation of memory phenotype $CD8^+$ T cells but are not required for memory phenotype $CD4^+$ T cells," *J Exp Med* 195(12):1523-1532, 2002.
Thomas et al., "Targeting the Wilms Tumor Antigen 1 by TCR Gene Transfer: TCR Variants Improve Tetramer Binding but Not the Function of Gene Modified Human T Cells," *The Journal of Immunology* 179:5803-5810, 2007.
Turtle et al., "A distinct subset of Self-Renewing Human Memory $CD8^+$ T Cells Survives Cytotoxic Chemotherapy," *Immunity* 31:834-844, Nov. 2009.
Uchida et al., "Primitive human hematopoietic cells displaying differential efflux of the rhodamine 123 dye have distinct biological activities," *Blood* 88(4):1297-1305, 1996.
Walker et al., "Interaction of Human IgG Chimeric Antibodies with the Human FcRI and FcRII Receptors: Requirements for Antibody-Mediated Host Cell-Target Cell Interaction," *Molecular Immunology* 26(4):403-411, 1989.
Walter et al., "$CD8^+$ T cells in autoimmunity," *Curr Opin Immunol* 17:624-631, 2005.
Walter et al., "Reconstitution of cellular immunity against cytomegalovirus in recipients of allogeneic bone marrow by transfer of T-cell clones from the donor," *N Engl J Med* 333:1038-1044, 1995.
Wulf et al., "A leukemic stem cell with intrinsic drug effluc capacity in acute myeloid leukemia," *Blood* 98(4):1166-1173, 2001.
Zhang et al., "Host-reactive $CD8^+$ memory stem cells in graft-versus-host-disease," *Nat Med* 11(12):1299-1305, 2005.

\* cited by examiner

SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: MDR1 Forward Primer

<400> SEQUENCE: 1
ggaagccaat gcctatgact tta                                    23

<210> SEQ ID NO 2
<211> LENGTH: 21
<212> TYPE: DNA
<213> ORGANISM: Artificial Sequence
<220> FEATURE:
<223> OTHER INFORMATION: MDR1 Reverse Primer

<400> SEQUENCE: 2
gaaccactgc ttcgctttct g                                      21

<210> SEQ ID NO 3
<211> LENGTH: 30
<212> TYPE: DNA
<213> ORGANISM: Artificial Sequence
<220> FEATURE:
<223> OTHER INFORMATION: MDR1 Probe

<400> SEQUENCE: 3
tgaaactgcc tcataaattt gacaccctgg                             30

<210> SEQ ID NO 4
<211> LENGTH: 9
<212> TYPE: PRT
<213> ORGANISM: Artificial Sequence
<220> FEATURE:
<223> OTHER INFORMATION: HLA-A201 Restricted peptides

<400> SEQUENCE: 4

Asn Leu Val Pro Met Val Ala Thr Val
1               5

<210> SEQ ID NO 5
<211> LENGTH: 9
<212> TYPE: PRT
<213> ORGANISM: Artificial Sequence
<220> FEATURE:
<223> OTHER INFORMATION: HLA-A201 Restricted peptides

<400> SEQUENCE: 5

Gly Leu Cys Thr Leu Val Ala Met Leu
1               5

<210> SEQ ID NO 6
<211> LENGTH: 9
<212> TYPE: PRT
<213> ORGANISM: Artificial Sequence
<220> FEATURE:
<223> OTHER INFORMATION: HLA-A201 Restricted peptides

<400> SEQUENCE: 6

Gly Ile Leu Gly Phe Val Phe Thr Leu
1               5

IDENTIFICATION OF CD8+ T CELLS THAT ARE CD161$^{hi}$ AND/OR IL18R($\alpha$)$^{hi}$ AND HAVE RAPID DRUG EFFLUX CAPACITY

STATEMENT OF GOVERNMENT INTEREST

This invention was made with government support under AI053193 and CA114536 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_423C1_SEQUENCE_LISTING.txt. The text file is 2 KB, was created on Feb. 15, 2018, and is being submitted electronically via EFS-Web.

BACKGROUND

Technical Field

The present invention concerns the utilization of high CD161 and/or IL-18R$\alpha$ expression to identify putative long-lived rhodamine 123-effluxing central (CM) and effector memory (EM) CD8+ T cells. The invention may have applications in adoptive T cell immunotherapy for cancer and infectious diseases, gene delivery, targeted ablation immunotherapy and compositions useful therein.

Description of the Related Art

The ability to specifically recognize, control and eliminate infections and cancer is one of the hallmarks of human immunity. The immune system can be partitioned into 1) the non-specific 'innate' system, with responses mediated by macrophages, dendritic cells, natural killer cells and neutrophils and recognizing a relatively small number of pathogen-associated molecular patterns, and 2) the highly specific CD4+ and CD8+ T cell-mediated 'adaptive' immune system, potentially recognizing millions of different peptide antigens.

Recognition of specific antigens by CD8+ T cells of the adaptive immune system is mediated by highly diverse T cell receptors (TCR). T cells bearing a single TCR can recognize a specific peptide antigen presented by an appropriate MHC molecule, resulting in an 'adaptive' immune response with specificity for the presented peptide antigen. The CD8+ T cell 'adaptive' immune response to 'foreign' antigens is well characterized in viral infection, but CD8+ T cells specific for mutated or non-mutated 'self' antigens may be found in other conditions such as cancer and autoimmune disease (1-7).

In acute viral infection, virus-derived antigens are processed and presented by antigen presenting cells (APC) to naïve T cells that express TCRs capable of recognizing the viral antigen and in humans are characterized by cell surface expression of CD45RA and CD62L and absence of CD95 expression. The activated antigen-specific naïve T cells then rapidly proliferate and differentiate into an effector T cell population. The vast majority of effector T cells subsequently die, but a small fraction survives and become memory T cells (8, 9). On re-challenge with the virus, the surviving memory T cell population has the capacity to rapidly proliferate and differentiate into an effector population to rapidly contain the infection and protect the host. Antigen-specific CD8+ T cell memory has been described to persist up to 75 years, even in the absence of antigen rechallenge—essentially providing immunity to that antigen for the lifetime of the host (10).

The surviving memory T cell population is highly heterogeneous and comprises three main subsets in humans termed central memory (CM), effector memory (EM) and effector memory RA+ (EM$_{RA}$). These subsets, and sub-populations thereof, differ in phenotype, ontogeny, homing, proliferative capacity and cytokine secretion, and might have distinct roles in maintenance of immune memory (11-13). The distribution of memory subsets can be affected by variation in conditions at priming such as the nature of the APC and antigen, the antigen density and the presence of cytokines, costimulatory molecules and inflammatory mediators (8). Once established, CD8+ T cell memory can persist in the absence of antigen (14, 15). Memory CD8+ T cell populations undergo homeostatic (steady state) proliferation and different subsets appear to have different rates of turnover in vivo (16). Interleukin-(IL-) 15 is a critical mediator of homeostatic proliferation and IL-7 is important for the survival of established memory responses (17-22). Despite advances in our understanding of the acute effector response to viral infection and the transition to a stable memory response, the mechanisms by which CD8+ memory is established and maintained have not been elucidated.

It has been hypothesized that a population of 'stem-cell' like T cells with the capacity to self-renew and differentiate into effectors may provide for the maintenance of immunologic memory (23). A putative memory stem cell was recently identified in a murine model of graft versus host disease (GVHD) (24). After secondary transfer from mice with GVHD, only post-mitotic CD8+/CD44$^{lo}$/CD62L$^{hi}$/Sca-1$^{hi}$ memory cells were able to initiate GVHD, give rise to memory (CM and EM) and effector subsets, and retain replicative potential. Another study in mice demonstrated asymmetric cell division, a characteristic stem cell self-renewal mechanism, after the first encounter of naïve T cells with antigen (25). After the first division, the progeny 'distal' and 'proximal' to the immunologic synapse were programmed for a memory and effector phenotype, respectively. These studies suggest that antigen-specific CD8+ T cell memory may be maintained by a long-lived population with stem cell features and the capacity to self-renew. To date, no candidate population has been identified in the human.

The identification of the phenotype of long-lived memory CD8+ T cells or memory stem cells will have profound implications for investigation and therapy of infections, cancer and autoimmune diseases. We have used multiparameter flow cytometry to identify memory CD8+ T cell populations in humans with features consistent with stem cell behavior and long survival. A characteristic of hematopoietic and cancer stem cells is the ability to efflux chemotherapy drugs and fluorescent dyes (26-30). We found that subpopulations of CM and EM CD8+ T cells also had the capacity to rapidly efflux fluorescent dyes and chemotherapy drugs and we hypothesized that these cells could be responsible for the observed chemoresistance of CD8+ T cell memory after severely myelosuppressive chemotherapy. In vitro studies demonstrated that CM and EM subsets with the capacity to rapidly efflux rhodamine 123 (Rh123) (referred to as CMhi and EMhi, respectively for high efflux capacity) were more resistant to apoptosis than their non-effluxing counterparts in response to cytotoxic chemotherapy and that chemoresistance was attenuated by blockade of ATP-binding cassette cotransporter efflux channels.

Gene expression profiling studies show that CMhi and EMhi CD8+ T cells comprise similar, yet distinct subsets. In addition, they have gene expression profiles that are unique and distinct from those of other memory or naïve CD8+ T cell populations. Further studies showed that the immunophenotype of Rh123 effluxing memory populations was similar to previously described 'memory stem cells' in mice and the 'distal pole-derived memory cells' after asymmetric division of naïve murine CD8+ T cells. CMhi and EMhi populations harbor CD8+ T cells expressing a polyclonal TCR repertoire and CMV, EBV and influenza antigen-specific CD8+ T cells can be identified within the subsets.

CMhi and EMhi CD8+ T cells are refractory to polyclonal stimulation with OKT3, demonstrating reduced proliferation and cytokine secretion, compared to non-effluxing CD8+ T cells. They also exhibit low intracellular calcium flux in response to ionomycin stimulation. The reduced proliferation and cytokine secretion can be partially rescued with costimulation and inflammatory cytokines. Despite the reduction in secretion of many inflammatory cytokines, CMhi and EMhi secreted IL-17 in response to PMA-ionomycin stimulation in contrast to other memory CD8+ T cell subsets.

The refractory nature of CMhi and EMhi may allow them to remain in a quiescent state, avoiding differentiation in response to antigenic stimulation in all but the most inflammatory conditions. The observations that CMhi show high $^3$H-thymidine uptake and CFSE dilution in response to the homeostatic cytokines, IL-7 and IL-15, suggests that these chemoresistant cells may proliferate during the lymphocyte nadir after myelosuppressive chemotherapy when IL-7 and IL-15 levels are elevated, and potentially repopulate the memory CD8+ T cell compartment.

CMhi and EMhi are found in very low numbers in cord blood. They are found in high numbers in early adulthood and decline with advancing age. A population that arises after antigen exposure in early life and is gradually exhausted with repeated inflammatory antigenic stimuli in adulthood would be consistent with a putative memory stem cell. It would also be consistent with recognized decreased efficacy of vaccination in elderly subjects.

Identification of CMhi and EMhi can be easily achieved in vitro using Rh123 efflux assays; however the use of Rh123 in functional studies or clinical grade isolation is problematic. Therefore, we used multiparameter flow cytometry to search for cell surface markers that might distinguish this subset of cells in human blood samples. We found that high expression of CD161 and/or IL-18Rα identifies subsets that are enriched in CMhi and EMhi, facilitating identification and isolation of these cells in the absence of in vitro culture or exposure of the cells to Rh123 toxicity.

There is extensive evidence suggesting that memory CD8+ T cells have a role in prevention, control and therapy of infections, cancer and autoimmune diseases (1-7). Clinical studies of CD8+ T cell adoptive transfer in stage IV melanoma resulted in up to 51% CR/PR and demonstrated that persistence of the transferred tumor-specific T cells was critical for efficacy (31, 32). Findings in CMV-specific adoptive transfer studies also demonstrated the need for persistence, strongly supporting the hypothesis that the establishment of long-lived memory responses may be essential for successful control and protection against tumors and infection by adoptive T cell transfer (33). These studies are complemented by work in mice, demonstrating the critical role of persistent memory CD8+ T cells in eliminating clinically apparent cancer and establishing healthy equilibrium in occult cancer (4).

Despite the evidence that perturbations in memory CD8+ T cells are important in disease processes, attempts to specifically ablate, augment or transfer antigen-specific immune memory have met with limited success. Clinical responses after transfer of CD8+ lines or clones have been shown previously, but have been sporadic, related to their unpredictable persistence in vivo (32). Recent studies in non-human primates have shown CM-derived CD8+ clones can persist for up to one year after infusion, whereas EM-derived clones die rapidly by apoptosis, despite the fact that both populations shared an effector phenotype prior to transfer (34). This suggests that effector CD8+ T cells may retain an intrinsic program, derived from their cell of origin, which determines their survival in vivo after antigenic stimulation and clonal expansion. The implication is that clones or lines must be generated from appropriately programmed subsets if transferred memory CD8+ T cells are to persist in vivo. CMhi and EMhi are subsets with characteristics that suggest they are programmed for long survival.

The identification of memory CD8+ T cell subsets with appropriate programming for persistence will facilitate transfer of CD8+ T cell-mediated immunity against specific antigens. CD8+ T cells with programming for persistence and long-lived survival may also be useful as delivery vehicles for therapeutic genes. In addition to being amenable to long-term survival for maintenance of therapeutic immunity or gene delivery after adoptive transfer, CMhi and EMhi long-lived memory cells may act as targets for immunosuppression by ablation of antigen-specific memory responses through the use of toxin-conjugated CD161 and/or IL-18Rα monoclonal antibodies. This form of therapy may have a role in autoimmune diseases and graft versus host disease.

REFERENCES

1. Galon, J., A. Costes, F. Sanchez-Cabo, A. Kirilovsky, B. Mlecnik, C. Lagorce-Pages, M. Tosolini, M. Camus, A. Berger, P. Wind, F. Zinzindohoue, P. Bruneval, P. H. Cugnenc, Z. Trajanoski, W. H. Fridman, and F. Pages. 2006. Type, density, and location of immune cells within human colorectal tumors predict clinical outcome. Science 313: 1960-1964.

2. Pages, F., A. Berger, M. Camus, F. Sanchez-Cabo, A. Costes, R. Molidor, B. Mlecnik, A. Kirilovsky, M. Nilsson, D. Damotte, T. Meatchi, P. Bruneval, P. H. Cugnenc, Z. Trajanoski, W. H. Fridman, and J. Galon. 2005. Effector memory T cells, early metastasis, and survival in colorectal cancer. N Engl J Med 353:2654-2666.

3. Beckhove, P., M. Feuerer, M. Dolenc, F. Schuetz, C. Choi, N. Sommerfeldt, J. Schwendemann, K. Ehlert, P. Altevogt, G. Bastert, V. Schirrmacher, and V. Umansky. 2004. Specifically activated memory T cell subsets from cancer patients recognize and reject xenotransplanted autologous tumors. J Clin Invest 114:67-76.

4. Koebel, C. M., W. Vermi, J. B. Swann, N. Zerafa, S. J. Rodig, L. J. Old, M. J. Smyth, and R. D. Schreiber. 2007. Adaptive immunity maintains occult cancer in an equilibrium state. Nature 450:903-907.

5. Michalek, J., I. Kocak, V. Fait, J. Zaloudik, and R. Hajek. 2007. Detection and long-term in vivo monitoring of individual tumor-specific T cell clones in patients with metastatic melanoma. J Immunol 178:6789-6795.

6. Walter, U., and P. Santamaria. 2005. CD8+ T cells in autoimmunity. Curr Opin Immunol 17:624-631.

7. Rezvani, K., J. M. Grube, J. M. Brenchley, G. Sconocchia, H. Fujiwara, D. A. Price, E. Gostick, K. Yamada, J. Melenhorst, R. Childs, N. Hensel, D. C. Douek, and A. J.

Barrett. 2003. Functional leukemia-associated antigen-specific memory CD8+ T cells exist in healthy individuals and in patients with chronic myelogenous leukemia before and after stem cell transplantation. *Blood* 102:2892-2900.

8. Prlic, M., M. A. Williams, and M. J. Bevan. 2007. Requirements for CD8 T-cell priming, memory generation and maintenance. *Curr Opin Immunol* 19:315-319.

9. Kaech, S. M., J. T. Tan, E. J. Wherry, B. T. Konieczny, C. D. Surh, and R. Ahmed. 2003. Selective expression of the interleukin 7 receptor identifies effector CD8 T cells that give rise to long-lived memory cells. *Nat Immunol* 4:1191-1198.

10. Hammarlund, E., M. W. Lewis, S. G. Hansen, L. I. Strelow, J. A. Nelson, G. J. Sexton, J. M. Hanifin, and M. K. Slifka. 2003. Duration of antiviral immunity after smallpox vaccination. *Nat Med* 9:1131-1137.

11. Lanzavecchia, A., and F. Sallusto. 2005. Understanding the generation and function of memory T cell subsets. *Curr Opin Immunol* 17:326-332.

12. Sallusto, F., J. Geginat, and A. Lanzavecchia. 2004. Central memory and effector memory T cell subsets: function, generation, and maintenance. *Annu Rev Immunol* 22:745-763.

13. Sallusto, F., D. Lenig, R. Forster, M. Lipp, and A. Lanzavecchia. 1999. Two subsets of memory T lymphocytes with distinct homing potentials and effector functions. *Nature* 401:708-712.

14. Murali-Krishna, K., L. L. Lau, S. Sambhara, F. Lemonnier, J. Altman, and R. Ahmed. 1999. Persistence of memory CD8 T cells in MHC class I-deficient mice. *Science* 286:1377-1381.

15. Jabbari, A., and J. T. Harty. 2005. Cutting edge: differential self-peptide/MHC requirement for maintaining CD8 T cell function versus homeostatic proliferation. *J Immunol* 175:4829-4833.

16. Geginat, J., A. Lanzavecchia, and F. Sallusto. 2003. Proliferation and differentiation potential of human CD8+ memory T-cell subsets in response to antigen or homeostatic cytokines. *Blood* 101:4260-4266.

17. Becker, T. C., E. J. Wherry, D. Boone, K. Murali-Krishna, R. Antia, A. Ma, and R. Ahmed. 2002. Interleukin 15 is required for proliferative renewal of virus-specific memory CD8 T cells. *J Exp Med* 195:1541-1548.

18. Schluns, K. S., W. C. Kieper, S. C. Jameson, and L. Lefrancois. 2000. Interleukin-7 mediates the homeostasis of naive and memory CD8 T cells in vivo. *Nat Immunol* 1:426-432.

19. Tan, J. T., B. Ernst, W. C. Kieper, E. LeRoy, J. Sprent, and C. D. Surh. 2002. Interleukin (IL)-15 and IL-7 jointly regulate homeostatic proliferation of memory phenotype CD8+ cells but are not required for memory phenotype CD4+ cells. *J Exp Med* 195:1523-1532.

20. Intlekofer, A. M., N. Takemoto, E. J. Wherry, S. A. Longworth, J. T. Northrup, V. R. Palanivel, A. C. Mullen, C. R. Gasink, S. M. Kaech, J. D. Miller, L. Gapin, K. Ryan, A. P. Russ, T. Lindsten, J. S. Orange, A. W. Goldrath, R. Ahmed, and S. L. Reiner. 2005. Effector and memory CD8+ T cell fate coupled by T-bet and eomesodermin. *Nat Immunol* 6:1236-1244.

21. Kennedy, M. K., M. Glaccum, S. N. Brown, E. A. Butz, J. L. Viney, M. Embers, N. Matsuki, K. Charrier, L. Sedger, C. R. Willis, K. Brasel, P. J. Morrissey, K. Stocking, J. C. Schuh, S. Joyce, and J. J. Peschon. 2000. Reversible defects in natural killer and memory CD8 T cell lineages in interleukin 15-deficient mice. *J Exp Med* 191:771-780.

22. Hand, T. W., M. Morre, and S. M. Kaech. 2007. Expression of IL-7 receptor alpha is necessary but not sufficient for the formation of memory CD8 T cells during viral infection. *Proc Natl Acad Sci USA* 104:11730-11735.

23. Fearon, D. T., P. Manders, and S. D. Wagner. 2001. Arrested differentiation, the self-renewing memory lymphocyte, and vaccination. *Science* 293:248-250.

24. Zhang, Y., G. Joe, E. Hexner, J. Zhu, and S. G. Emerson. 2005. Host-reactive CD8+ memory stem cells in graft-versus-host disease. *Nat Med* 11:1299-1305.

25. Chang, J. T., V. R. Palanivel, I. Kinjyo, F. Schambach, A. M. Intlekofer, A. Banerjee, S. A. Longworth, K. E. Vinup, P. Mrass, J. Oliaro, N. Killeen, J. S. Orange, S. M. Russell, W. Weninger, and S. L. Reiner. 2007. Asymmetric T lymphocyte division in the initiation of adaptive immune responses. *Science* 315:1687-1691.

26. McKenzie, J. L., K. Takenaka, O. I. Gan, M. Doedens, and J. E. Dick. 2007. Low rhodamine 123 retention identifies long-term human hematopoietic stem cells within the Lin-CD34+CD38- population. *Blood* 109:543-545.

27. Uchida, N., J. Combs, S. Chen, E. Zanjani, R. Hoffman, and A. Tsukamoto. 1996. Primitive human hematopoietic cells displaying differential efflux of the rhodamine 123 dye have distinct biological activities. *Blood* 88:1297-1305.

28. Wulf, G. G., R. Y. Wang, I. Kuehnle, D. Weidner, F. Marini, M. K. Brenner, M. Andreeff, and M. A. Goodell. 2001. A leukemic stem cell with intrinsic drug efflux capacity in acute myeloid leukemia. *Blood* 98:1166-1173.

29. Schinkel, A. H., and J. W. Jonker. 2003. Mammalian drug efflux transporters of the ATP binding cassette (ABC) family: an overview. *Adv Drug Deliv Rev* 55:3-29.

30. Elliott, J. I., S. Raguz, and C. F. Higgins. 2004. Multidrug transporter activity in lymphocytes. *Br J Pharmacol* 143:899-907.

31. Robbins, P. F., M. E. Dudley, J. Wunderlich, M. El-Gamil, Y. F. Li, J. Zhou, J. Huang, D. J. Powell, Jr., and S. A. Rosenberg. 2004. Cutting edge: persistence of transferred lymphocyte clonotypes correlates with cancer regression in patients receiving cell transfer therapy. *J Immunol* 173:7125-7130.

32. Dudley, M. E., J. R. Wunderlich, J. C. Yang, R. M. Sherry, S. L. Topalian, N. P. Restifo, R. E. Royal, U. Kammula, D. E. White, S. A. Mavroukakis, L. J. Rogers, G. J. Gracia, S. A. Jones, D. P. Mangiameli, M. M. Pelletier, J. Gea-Banacloche, M. R. Robinson, D. M. Berman, A. C. Filie, A. Abati, and S. A. Rosenberg. 2005. Adoptive cell transfer therapy following non-myeloablative but lymphodepleting chemotherapy for the treatment of patients with refractory metastatic melanoma. *J Clin Oncol* 23:2346-2357.

33. Walter, E. A., P. D. Greenberg, M. J. Gilbert, R. J. Finch, K. S. Watanabe, E. D. Thomas, and S. R. Riddell. 1995. Reconstitution of cellular immunity against cytomegalovirus in recipients of allogeneic bone marrow by transfer of T-cell clones from the donor. *N Engl J Med* 333:1038-1044.

34. Berger, C., M. C. Jensen, P. M. Lansdorp, M. Gough, C. Elliott, and S. R. Riddell. 2008. Adoptive transfer of effector CD8+ T cells derived from central memory cells establishes persistent T cell memory in primates. *J Clin Invest* 118:294-305.

BRIEF SUMMARY

Identification of long-lived memory cells in humans has not been possible to date. We demonstrate that high CD161 and/or IL-18Rα expression may be used to identify human Rh123 effluxing long-lived memory cells in the CM and/or EM CD8+ T cell compartments. These populations may be useful as a source of T cells for adoptive immunotherapy, gene delivery or as targets for ablation in autoimmune or other immunopathologic conditions.

This invention provides methods for the identification and isolation of viable putative long-lived antigen-specific memory CD8$^+$ T cell subsets (CMhi and EMhi) with high surface expression of CD161 and/or IL-18Rα and the capacity to rapidly efflux the fluorescent dye Rh123.

We propose that CMhi and EMhi cells are programmed for long in vivo survival and chemoresistance, consistent with their shared characteristics with stem cell populations in other tissues. The identification of a distinguishing phenotype, including the high surface expression of CD161 and/or IL-18Rα will enable the isolation and in vitro manipulation of these T cell subsets. The ability to isolate and adoptively transfer long-lived T cells in an autologous, allogeneic or syngeneic setting may enable transfer of persistent antigen-specific immunity. This may be important in a range of applications, including, but not limited to prevention, control or elimination of cancer or infection. Alternatively, targeted ablation of CMhi and EMhi populations may result in potent immunosuppression and treatment of autoimmune diseases or graft versus host disease. Candidate immunomodulatory therapies, such as vaccines or immunosuppressant drugs, may be screened in high throughput in vitro assays using the invention. The invention may also be used as an in vivo delivery vehicle for therapeutic genes.

Stated otherwise, a first aspect of the invention is a human CD8$^+$ T lymphocyte that has high expression of CD161 and/or IL-18Rα (e.g., a lymphocyte that actively effluxes Rh123 in less than 30 minutes culture in RPMI 1640/10% BSA at 37° C. (a "rapidly effluxing and/or CD161$^{hi}$ and/or IL-18Rα$^{hi}$ T lymphocyte"). The lymphocytes may be provided in isolated, enriched and/or purified form.

In some embodiments, the lymphocyte is TCRαβ$^+$, TCRγδ$^-$, CD8α$^{hi/int}$, CD8β$^{hi/int/neg}$, CD45RA$^{int/neg}$, CD45RO$^{int/hi}$, CD95$^{int/hi}$, CD25$^{int/neg}$, CD27$^+$, CD28$^+$, CD57$^-$, CD127$^+$ CD103$^-$, PD-1$^{neg}$, bcl-2$^{hi}$, bcl-xL$^{hi}$, perforin$^{int}$, granzyme A$^{int}$, granzyme B$^{int/neg}$ and NKG2D$^{int}$.

In some embodiments, the lymphocyte has high expression of MDR-1 mRNA.

In some embodiments, the lymphocyte has the capacity to actively efflux the fluorescent chemotherapy drug, daunorubicin.

In some embodiments, the lymphocyte is resistant to apoptosis after culture with 0.03-0.3 μM daunorubicin and such resistance is abrogated by the efflux inhibitor PK11195.

In some embodiments, the lymphocyte demonstrates absent or lower proliferation in response to stimulation with 250-1000 ng/ml plate-bound OKT3 than its non-effluxing counterpart T lymphocyte. The reduced proliferation can be partially recovered by costimulation with plate-bound anti-CD28 antibody and/or addition of cytokines including, but not limited to, IL-7, IL-12, IL-15, IL-18 and IL-23 or combinations thereof.

In some embodiments, the lymphocyte has reduced secretion of IFN-γ, IL-2, IL-4, IL-5, IL-8, IL-10 and MIP-1α compared to their non-effluxing counterparts in response to stimulation with PMA/ionomycin or OKT3 in combination with anti-CD28 antibody or cytokines.

In some embodiments, the lymphocyte has low, but heterogeneous, calcium flux after stimulation with ionomycin;

In some embodiments, the lymphocyte is a CD62L$^+$ central memory T cell.

In some embodiments, the lymphocyte demonstrates high uptake of $^3$H-thymidine in response to 4 days culture with 0.5-2.0 ng/ml IL-7 and greater dilution of CFSE in response to 8-11 days culture with 0.5-2.0 ng/ml IL-7, as compared to its non-effluxing counterpart T lymphocyte.

In some embodiments, the lymphocyte is a CD62L$^-$ effector memory T cell.

A further aspect of the invention is lymphocytes as described herein for use in adoptive immunotherapy or gene therapy, or for use in the preparation of a medicament for adoptive immunotherapy or gene therapy.

A further aspect of the invention is a composition comprising, consisting of or consisting essentially of lymphocytes as described herein in a pharmaceutically acceptable carrier.

A further aspect of the invention is a method of treating a human subject in need thereof, comprising administering lymphocytes as described herein to the said subject in a treatment-effective amount. The lymphocytes may be autologous, allogeneic, or syngeneic cells. The method may be carried out for immunotherapy or adoptive immunotherapy; the method may be carried out where the subject is afflicted with at least one of: cancer, infectious disease, or iatrogenic or congenital immunodeficiency; the method may be carried out for gene therapy; the method may be carried out where the subject is afflicted with one of: congenital genetic disorder, cancer, infectious disease, or iatrogenic or congenital immunodeficiency. A typical example of the use of the invention in adoptive immunotherapy would be treatment in the setting of allogeneic or autologous hematopoietic stem cell transplantation (HSCT). In the setting of severe immunosuppression, allogeneic and autologous HSCT patients are at great risk of contracting opportunistic infections. The invention may be used to transfer immune memory to the recipient to protect them against potentially life-threatening infection. CMhi and EMhi cells may be isolated from the transplant donor (in the case of allogeneic HSCT) or the patient (in the case of autologous HSCT), selected or engineered for specificity to infection-associated antigens, expanded or not, and returned to the patient in the post transplant setting. The subsets would proliferate with or without differentiation in the post-transplant lymphopenic environment and reconstitute immune memory. The selection of CMhi and EMhi specific for infections would allow reconstitution of immunity without causing graft versus host disease.

A further aspect of the invention is a method of treating a human subject in need thereof, comprising ablating rapidly effluxing and/or CD161 and/or IL-18Rα$^{hi}$ T lymphocytes in said subject by a treatment-effective amount. The ablating step can be carried out in vivo or in vitro. In some embodiments, the subject is afflicted with or at risk for at least one of: of autoimmune disease, graft versus host disease or rejection of a transplant graft. In some embodiments the ablating step is carried out in vivo by direct treatment of the patient; in some embodiments the ablating step is carried out ex vivo by depletion of cells from a cellular product or extracorporeal circulation; in some embodiments the ablating step is carried out by ablating said cells from a transplant graft prior to transplantation. In some embodiments the ablating step is carried out by administering anti-CD161 and/or anti-IL-18Rα monoclonal or polyclonal antibodies, conjugated or not to toxic groups or radioisotopes, lymphotoxic drug treatment with inhibition of efflux pumps, or combinations thereof.

A further aspect of the invention is a kit for the identification or isolation of rapidly effluxing T lymphocytes as described herein, comprising a combination of at least two, three or four, in any combination, of: (a) a combination of fluorochrome-conjugated antibodies to allow identification of central and effector memory CD8+ T cells; (b) a fluorochrome-conjugated antibody to CD161 and/or IL-18Rα and appropriate isotype control; (c) Rh123 and a negative control antagonist of Rh123 efflux; (d) appropriate assay medium; and (e) instructions and packaging.

The foregoing and other objects and aspects of the present invention are explained in greater detail in the drawings herein and the specification below.

Figure 1:
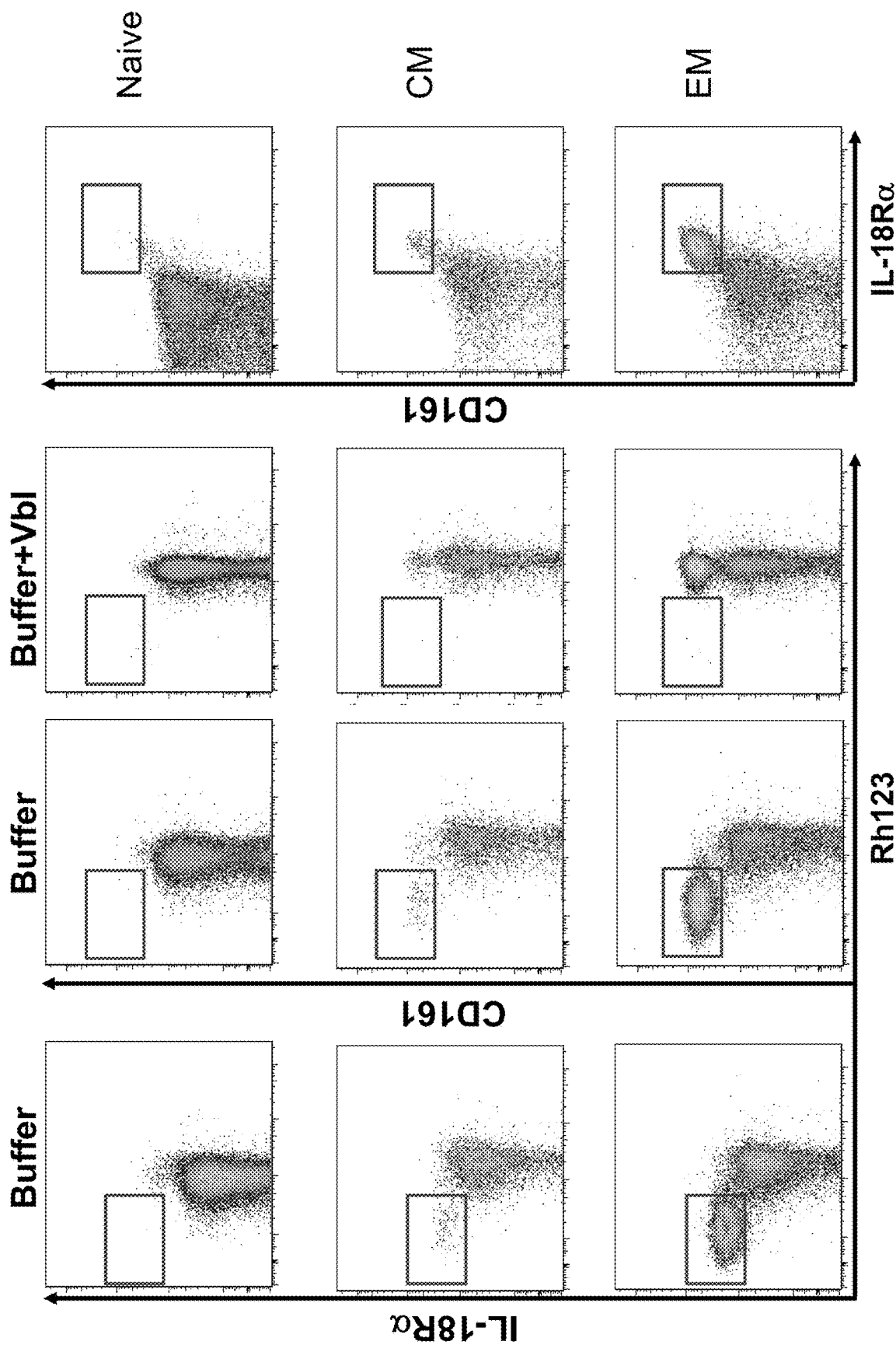
FIG. 1: CM and EM populations contain subsets that rapidly efflux Rh123 and are CD161$^{hi}$ and IL-18Rα$^{hi}$ as described in Example 1.

The present invention is explained in greater detail below. The disclosures of all United States patent references cited herein are incorporated by reference herein in their entirety.

DETAILED DESCRIPTION

I. Definitions

"T cells" or "T lymphocytes" as used herein are from humans. In some embodiments the T cells are autologous (the donor and the recipient are the same individual); in some embodiments the T cells are allogeneic (the donor and recipient/s are genetically different individuals); in some embodiments the T cells are syngeneic (the donor and recipient/s are different individuals who are genetically identical).

"Cytotoxic T lymphocyte" (CTL) as used herein refers to a T lymphocyte that expresses CD8 on the surface thereof (i.e., a CD8+ T cell).

"Central memory" T cell (or "CM") as used herein refers to a CTL that has previously been exposed to antigen (a "memory CTL") and is CD62L+, CD45RA$^{int/neg}$/CD45RO$^{int/hi}$ and CD95$^{int/hi}$.

"Effector memory" T cell (or "EM") as used herein refers to a CTL that has previously been exposed to antigen (a "memory CTL") and is CD62L−, CD45RA$^{int/neg}$/CD45RO$^{int/hi}$ and CD95$^{int/hi}$.

"Rapidly effluxing T lymphocytes" are found within the CD8+ T cell CM and EM populations (CMhi and EMhi, respectively) with some or all of the following identifying characteristics: (a) actively and rapidly efflux the dye Rh123 in culture over a time of 30 minutes at a temperature of 37° C.; (b) high surface expression of CD161 (CD161$^{hi}$) and/or IL-18Rα (IL-18Rα$^{hi}$). Such cells typically include, but are not limited to, the following features: (a) high surface expression of CD127, CD28; (b) typically, but not consistently, expression of markers suggesting derivation from the distal pole complex or uropod of mitotic CD8+ T cells (higher CD43, CD44, CD46, CD148 and CD162 surface expression than non-effluxing subsets; lower CD8, CD11a and CD50 surface expression than non-effluxing subsets); (c) CD3+/TCRαβ+/TCRγδ−; (d) low or no surface expression of CD25, CD57, PD-1, CD103 and CD69; (e) lower surface expression of NKG2D than non-effluxing subsets; (f) intermediate/high expression of CD45RO, intermediate/negative surface expression of CD45RA and expression of CD95; (g) typically, but not consistently higher expression of bcl-2 and bcl-xL than their non-effluxing counterparts; (h) negative expression of granzyme B, intermediate expression of granzyme A and low/intermediate expression of perforin; (i) normal or low expression of CD8α and normal, low or absent expression of CD8β; (j) higher expression of MDR-1 mRNA than their non-effluxing counterparts; (k) lower percentage expression of Ki67 than their non-effluxing counterparts in a healthy individual. Optionally, in some embodiments, rapidly effluxing T lymphocytes are characterized by positive surface expression of CD122. Note also that CD62L expression is variable and defines the presence of these cells in the CM or EM subsets. Such cells also typically include, but are not limited to, the following functional features: (a) low proliferation compared to non-effluxing subsets in response to stimulation with plate-bound OKT3, which can be increased after costimulation with anti-CD28 antibody or cytokines; (b) contain virus-specific clones, evidenced by tetramer binding and the capacity to identify antigen-specific CD8+ T cells after in vitro expansion of sorted subsets; (c) resistance to apoptosis during in vitro culture in the presence or absence of chemotherapeutic agents; (d) reduced secretion of IFN-γ, IL-2, IL-4, IL-5, IL-8, IL-10 and MIP-1α compared to their non-effluxing counterparts in response to stimulation with PMA/ionomycin or OKT3 in combination with anti-CD28 antibody or cytokines; (e) capacity to actively efflux the fluorescent chemotherapy drug, daunorubicin; (f) low, but heterogeneous, calcium flux after stimulation with ionomycin; (g) CMhi cells typically have an increased uptake of tritiated thymidine ($^3$H-thymidine) and increased dilution of CFSE compared to their non-effluxing counterparts in response to IL-7.

"Efflux blockers" as used herein includes, but is not limited to, PK11195, cyclosporine A, PSC833, verapamil.

"Effluxed drug" as used herein includes, but is not limited to, doxorubicin, daunorubicin, epirubicin, methotrexate, mitoxantrone, vinblastine, vincristine, dexamethasone and derivatives, etoposide and taxanes.

"Antigen" as used herein refers to a protein or peptide that can be recognized by the immune system.

"Antigen-specific" as used herein refers to the nature of the highly specific recognition by the adaptive immune system of peptide fragments presented in the context of an MHC molecule.

"Antibody" as used herein refers to all types of immunoglobulins, including IgG, IgM, IgA, IgD, and IgE and all isotypes thereof. Of the immunoglobulins, IgM and IgG are particularly preferred. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26, 403-11 (1989). The antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in SegAl et al., U.S. Pat. No. 4,676,980.

"Autoimmune disease" as used herein may be any autoimmune disease, including but not limited to: systemic lupus erythematosus, Hashimoto's disease, rheumatoid arthritis, graft-versus-host disease, Sjogren's syndrome, pernicious anemia, Addison's disease, scleroderma, Goodpasture's syndrome, Crohn's disease, autoimmune hemolytic anemia, sterility, myasthenia gravis, multiple sclerosis, Basedow's disease, thrombotic thrombocytopenic purpura, immune thrombocytopenic purpura, insulin-dependent diabetes mellitus, allergy, asthma, atopic disease, arteriosclerosis, myocarditis, cardiomyopathy, nephritis, and hypoplastic anemia. See, e.g., U.S. Pat. No. 7,279,160.

"Cancer" as used herein may include, but is not limited to any pathologic variation of: cancer of the prostate, breast, bladder, stomach, oropharynx, nasopharynx, esophagus, stomach, pancreas, liver, kidneys, colon, rectum, anus, lung, thyroid, brain, hematopoietic system (including, but not limited to Hodgkin's and Non-Hodgkin's lymphoma, acute and chronic lymphoid and myeloid leukemias) and skin (including, but not limited to, basal cell carcinoma, squamous cell carcinoma and melanoma).

"Donor" as used herein refers to the individual from whom rapidly effluxing T lymphocytes or other cellular product was obtained.

"Recipient" as used herein refers to the individual who will receive rapidly effluxing T lymphocytes or other treatment.

"Enriched" as used herein to describe amounts of cell types in a mixture refers to the subjecting of the mixture of the cells to a physical process or step, which results in an increase in the number of the "enriched" type, as compared to the same mixture before that physical process or step. For cell types that are few in number, those cells may be enriched five, ten, twenty, thirty, forty, or fifty fold (times) or more, yet still be a relatively small number of total cells (e.g., total number T cells) in the "enriched" population (e.g., the enriched cells being at least 1, 5, 10, 20, or 30 percent of the total cells in the preparation, or more, up to 40 or 50 percent of the total cells in the preparation or more). In other embodiments, the "enriched" cells may be enriched to a point that they become at least 40, 50, 60, 70 or 80 percent of the total cells in the preparation, or more, up to 90, 95, or 99 percent of the total cells in the preparation, or more).

"Toxic agent" as used herein includes, but is not limited to, radioisotopes, therapeutic drugs, and toxins or cytotoxins. See, e.g., U.S. Pat. No. 6,274,118.

"Radioisotope" as used herein includes but is not limited to. $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Therapeutic drug" as used herein includes but is not limited to Adriamycin, Chlororambucil, Daunorubicin, Leucovorin, Folinic acid, Methotrexate, Mitomycin C, Neocarzinostatin, Melphalan Vinblastine, Mitocyn, Mechlorethamine, Fluorouracil, Floxuridine, Idarubicin, Doxorubicin, Epirubicin, Cisplatin, Cannustine, Cyclophosphamide, Bleomycin, Vincristine and Cytarabine.

"Toxin" or "cytotoxin" as used herein includes but is not limited to diptheria toxin, ricin toxin, monensin, verrucarin A, abrin, saporin, vinca alkaloids, tricothecenes, and pseudomonas exotoxin A, and pokeweed viral protein. See, e.g., U.S. Pat. No. 6,630,576.

"Pharmaceutically acceptable" as used herein means that the compound or composition is suitable for administration to a subject to achieve the treatments described herein, without unduly deleterious side effects in light of the severity of the disease and necessity of the treatment.

II. Identification

Identification of Rh123-Effluxing CM and EM Populations. PBMC or T lymphocytes from any tissue can be collected in accordance with known techniques and loaded with Rh123 (or alternate similarly-effluxed fluorescent dye) at 5-10 µg/ml in RPMI 1640/10% BSA (efflux buffer) on ice for 30 minutes, washed three times and cultured in efflux buffer for 30 minutes at 37° C. A control sample cultured in the presence of vinblastine (a competitive antagonist of Rh123 efflux) can be used to establish and gate active efflux of Rh123. The PBMC can then be surface labeled with fluorochrome-conjugated antibodies (e.g., to CD4, CD16, TCRγδ, Vα24, CD8α, CD95 and CD62L), allowing identification of Rh123$^{lo}$ effluxing CM or EM populations by fluorescence-activated cell sorting (FACS) analysis.

Identification of CD161$^{hi}$ and/or IL-18Rα$^{hi}$ CM and EM Populations. High expression of CD161 and/or IL-18Rα on CM and EM populations can be used as a surrogate marker for the ability to rapidly efflux Rh123 in in vitro culture. T lymphocytes can be collected in accordance with known techniques from any tissue and labeled with fluorochrome-conjugated antibodies to CD161 and/or IL-18Rα, and other markers (e.g., to CD4, CD16, TCRγδ, Vα24, CD8α, CD95 and CD62L), allowing identification of CD161$^{hi}$ and/or IL-18Rα$^{hi}$ effluxing CM (CMhi) or EM (EMhi) populations by fluorescence-activated cell sorting (FACS) analysis.

III. Isolation

Isolation of Rh123-Effluxing CM and EM Populations. PBMC or T lymphocytes from any tissue can be collected in accordance with known techniques and enriched or depleted by known techniques such as affinity binding to antibodies such as in flow cytometry, immunomagnetic separation and/or affinity binding. For example, CD8+ CTL may be isolated by positive immunomagnetic separation. The positively selected CD8+ T cell fraction can be loaded with Rh123 (or alternate similarly-effluxed fluorescent dye) at 5-10 μg/ml in efflux buffer on ice for 30 minutes, washed three times and cultured in efflux buffer for 30 minutes at 37° C. A control sample cultured in the presence of vinblastine (a competitive antagonist of Rh123 efflux) can be used to establish and gate active efflux of Rh123. The PBMC can then be labeled with antibodies (e.g., to CD4, CD16, TCRγδ, Vα24, CD8α, CD95 and CD62L), allowing identification and isolation of CD4$^-$/CD16$^-$/TCRγδ$^-$/Vα24$^-$/CD8α$^+$/CD95$^+$/CD62L$^+$/Rh123$^{lo}$ effluxing CMhi or CD4$^-$/CD16$^-$/TCRγδ$^-$/Vα24$^-$/CD8α$^+$/CD95$^+$/CD62L$^-$/Rh123$^{lo}$ effluxing EMhi populations by fluorescence-activated cell sorting (FACS) analysis.

Isolation of CD161$^{hi}$ and/or IL-18Rα$^{hi}$ CM and EM Populations. High expression of CD161 and/or IL-18Rα on CM and EM populations can be used as a surrogate marker for the ability to rapidly efflux Rh123 in in vitro culture. T lymphocytes from any tissue can be collected in accordance with known techniques and enriched or depleted by known techniques such as affinity binding to antibodies such as in flow cytometry, immunomagnetic separation and/or affinity binding. For example, CD8+ CTL may be isolated by positive immunomagnetic separation. The positively selected CD8+ T cell fraction can be labeled with antibodies (e.g., to CD4, CD16, TCRγδ, Vα24, CD8α, CD95, CD62L and CD161 and/or IL-18Rα), allowing identification and isolation of CD4$^-$/CD16$^-$/TCRγδ$^-$/Vα24$^-$/CD8α$^+$/CD95$^+$/CD62L$^+$/CD161$^{hi}$ or CD4$^-$/CD16$^-$/TCRγδ$^-$/Vα24$^-$/CD8α$^+$/CD95$^+$/CD62L$^+$/IL-18Rα$^{hi}$ effluxing CMhi or CD4$^-$/CD16$^-$/TCRγδ$^-$/Vα24$^-$/CD8α$^+$/CD95$^+$/CD62L$^-$/CD161$^{hi}$ or CD4$^-$/CD16$^-$/TCRγδ$^-$/Vα24$^-$/CD8α$^+$/CD95$^+$/CD62L$^-$/IL-18Rα$^{hi}$ effluxing EMhi populations by fluorescence-activated cell sorting (FACS) analysis.

IV. Kits. Kits useful for carrying out all or parts of the methods of the invention (particularly the steps of identifying or isolating cell populations) may take any of a variety of forms. Typically the kits would include the necessary antibodies or antibody conjugates for the procedure. Isolation of these cells is a multistep process. Many combinations of kits are possible, depending on the desired product (pure CD8+ CMhi cells, pure CD8+ EMhi cells or enriched CD8+ CMhi and EMhi cells) and method of identification of CMhi and EMhi (Rh123 effluxing and/or CD161$^{hi}$ and/or IL-18Rα$^{hi}$). The kit may be used for identification and analysis, non-clinical grade or clinical grade isolation of Rh123 effluxing or non-effluxing populations. The kit can be packaged in any suitable container and optionally include instructions for carrying out all or parts of the methods described herein. Hence, a kit could include, but is not limited to, any components necessary for any combination of the following steps:

(i) Initial identification, enrichment and/or isolation of memory CD8+ T cells (positive or negative immunomagnetic selection or cell sorting)

(ii) Removal of contaminating cells after immunomagnetic separation (e.g., antibodies to non-CD8+ T cells, streptavidin-fluorochrome conjugates, goat anti-mouse-fluorochrome conjugates).

(iii) Identification, enrichment and/or isolation of CM and EM subsets (e.g., fluorochrome-conjugated CD95 and CD62L)

(iv) Identification, enrichment and/or isolation of effluxing (Rh123/efflux buffer/efflux blocking agents) or CD161$^{hi}$ and/or IL-18Rα$^{hi}$ populations V. Compositions and Methods for Therapy CMhi and EMhi cells may be used in an autologous, allogeneic or syngeneic setting. CMhi and EMhi populations may be used or targeted for, but are not limited to, the following indications;

(a) for transfer of antigen-specific immunity in cancer, infectious diseases or immunodeficiency (b) for targeted ablation of immunity in autoimmune diseases, graft versus host disease or graft rejection (c) for therapeutic gene delivery VI. Transfer of Antigen-Specific Immunity In some embodiments, the lymphocytes of the invention may be used to confer immunity to individuals. By "immunity" is meant an increase of one or more factors associated with a response to infection by a pathogen, or to a tumor, to which the lymphocyte response is directed.

Subjects that can be treated by the present invention are human. The subjects can be male or female and can be any suitable age, including infant, juvenile, adolescent, adult, and geriatric subjects.

Subjects that can be treated include subjects afflicted with cancer, including but not limited to hematopoietic cancers, cancers of the colon, lung, liver, breast, prostate, ovary, skin (including melanoma), bone, and brain etc. In some embodiments the tumor associated antigens are known, including, but not limited to melanoma, breast cancer, squamous cell carcinoma, colon cancer, leukemia, myeloma and prostate cancer (in these embodiments memory T cells can be isolated or engineered by introducing the T cell receptor genes). In other embodiments the tumor associated antigens can be targeted with genetically modified T cells expressing an engineered immunoreceptor. Examples include but are not limited to B cell lymphoma, breast cancer, prostate cancer, and leukemia.

Subjects that can be treated also include subjects afflicted with, or at risk of developing, an infectious disease, including but not limited to viral, bacterial, and protozoal infections.

Subjects that can be treated include immunodeficient patients, including but not limited to transplant patients, afflicted with a viral infection. Such viral infections may include, but are not limited to, cytomegalovirus (CMV), Epstein-Barr virus (EBV), adenovirus, influenza or parainfluenza, varicella, human herpes virus type 6 (HHV6) or HHV7, respiratory syncytial virus (RSV) or BK polyomavirus infections.

Cells prepared as described above can be utilized in methods and compositions for adoptive immunotherapy in accordance with known techniques, or variations thereof that will be apparent to those skilled in the art based on the instant disclosure (see, e.g., US Patent Application Publication No. 2003/0170238 to Gruenberg et al; see also U.S. Pat. No. 4,690,915 to Rosenberg; see also U.S. Pat. No. 6,040,177 to Riddell).

CMhi and EMhi may be used for therapy of autologous, allogeneic or syngeneic recipients and may be harvested in the presence or absence of in vivo stimulation, and administered with or without in vitro manipulation or in vivo stimulation after administration.

In vivo stimulation before harvesting CMhi and/or EMhi may involve, but is not limited to, the use of drugs, vaccines or cytokines. In vitro manipulation may involve, but is not limited to, by culture or other methods, any combination of subset enrichment, antigen-specific enrichment, expansion, feeder cell (e.g., irradiated LCL or PBMC) treatment, cytokine treatment, antibody treatment, small molecule treatment or transduction with antigen-specific TCR genes or other therapeutic, suicide and/or knockdown genes. In vivo stimulation may involve, but is not limited to, vaccination with commercial vaccines or research cellular or non-cellular reagents, cytokine administration or drug administration.

CMhi or EMhi cells may be infused with or without isolation and enrichment. The use and method of enrichment or isolation will reflect the requirements of the product. In some embodiments, the cells are formulated by first harvesting them from the donor or their culture medium, and then washing and concentrating the cells in a medium and container system suitable for administration (a "pharmaceutically acceptable" carrier) in a treatment-effective amount. Suitable infusion medium can be any isotonic medium formulation, such as normal saline, Normosol R (Abbott), Plasma-Lyte A (Baxter), 5% dextrose in water or Ringer's lactate. The infusion medium can be supplemented with human serum albumin, human serum or other nutrients.

The amount of cells to be infused is variable and may range from <10 antigen-specific cells in the absence of enrichment or in vitro expansion to greater than $10^{12}$ cells after enrichment and in vitro expansion (see, e.g., U.S. Pat. No. 6,040,177 to Riddell et al. at column 17). The cells may be administered by a single infusion or by multiple infusions over a range of time. However, since different individuals are expected to vary in responsiveness, the type and amount of cells infused, the route of administration, the number of infusions and the time range over which multiple infusions are given are determined by the attending physician as dictated by circumstance, physical and laboratory examination.

A typical example of the use of the invention in adoptive immunotherapy would be treatment in the setting of allogeneic or autologous hematopoietic stem cell transplantation (HSCT). In the setting of severe immunosuppression, allogeneic and autologous HSCT patients are at great risk of contracting opportunistic infections. The invention may be used to transfer immune memory to the recipient to protect them against potentially life-threatening infection. CMhi and EMhi cells may be isolated from the transplant donor (in the case of allogeneic HSCT) or the patient (in the case of autologous HSCT), selected or engineered for specificity to infection-associated antigens, expanded or not, and returned to the patient in the post transplant setting. The subsets would proliferate with or without differentiation in the post-transplant lymphopenic environment and reconstitute immune memory. The selection of CMhi and EMhi specific for infections would allow reconstitution of immunity without causing graft versus host disease.

VII. Targeted Ablation

A further aspect of the invention is a method of ablating long-lived memory CD8$^+$ T cells in a human subject by selectively depleting actively effluxing CMhi and/or EMhi cells in the subject as treatment for autoimmune disease or graft versus host disease. The selective depletion may be carried out by any suitable technique, such as by administering to the subject an antibody that selectively binds to CD161 and/or IL-18Rα in an amount effective to treat the disease or by administering inhibitors of drug efflux in combination with cytotoxic drugs.

The antibody, either monoclonal or polyclonal of any isotype, or pharmaceutical composition containing the same, can be formulated in multiple different carriers, or conjugated to many possible toxins, including but not limited to radioisotopes, ricin or diphtheria toxin, as is known in the art. The antibody could be administered by various routes including but not limited to, intravenously, intraperitoneally or intracisternally. A therapeutic antibody of the invention is administered in an effective amount to treat the disease, at a suitable schedule, though these will vary somewhat with the particular disease, formulation, route of administration, and condition of the subject, as is known in the art.

CMhi and EMhi may be ablated by administration of cytotoxic drugs in combination with inhibitors of cytotoxic drug efflux. In vitro studies show that CMhi and EMhi are protected from chemotherapy-induced apoptosis and this protection is lost in the presence of ABC-cotransporter (drug efflux pump) inhibition. Prevention of cytotoxic drug efflux from CMhi and EMhi may be used to reduce or ablate these cell populations in vivo. Cytotoxic drugs and drug efflux inhibitors may be administered in recognized or novel protocols as is known in the art.

VIII. Therapeutic Gene Delivery

In some embodiments, the lymphocytes of the invention may be used to deliver therapeutic genes to individuals. Therapeutic genes could include, but are not limited to, genes encoding costimulatory (e.g., CD80) or inhibitory molecules (PD-L1), cytokines (e.g., IL-7), apoptosis-inducing signals or congenitally deficient or abnormal genes (e.g., Factor VIII gene in severe hemophilia). The delivery of T cells transfected with genes encoding antigen-specific TCR is discussed above in "Transfer of antigen-specific immunity".

Isolation, in vitro manipulation, formulation and administration for therapeutic gene delivery will encompass similar considerations, as discussed above in "Transfer of antigen-specific immunity". Gene delivery to isolated T cells would likely be performed in vitro, but may include methods to target long-lived memory cells in vivo. Utilizing recombinant infectious virus particles for gene delivery is a preferred approach to the transduction of T lymphocytes of the present invention. The viral vectors which have been used in this way include virus vectors derived from simian virus 40, adenoviruses, adeno-associated virus (AAV), retroviruses and lentiviruses and modifications thereof. Thus, gene transfer and expression methods are numerous but essentially function to introduce and express genetic material in mammalian cells. Several of the above techniques, amongst others, have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation, retroviral infection and lentiviral infection.

EXPERIMENTAL

Example 1

CM and EM Populations Contain Subsets That Rapidly Efflux Rh123 and are CD161$^{hi}$ and IL-18Rα$^{hi}$ PBMC were separated from fresh peripheral blood by density gradient centrifugation, washed in RPMI 1640/10% bovine serum albumin (herein known as efflux buffer) and resuspended at $1\times10^6$/ml in ice cold efflux buffer with 10 μg/ml Rh123. PBMC were incubated for 30 minutes on ice before washing three times in ice cold efflux buffer and resuspending in pre-warmed efflux buffer, with or without vinblastine, for 30 minutes at 37° C. At 30 minutes, PBMC were washed once in ice cold PBS/0.2% BSA (FACS buffer) and labeled with antibodies to CD4, CD16, TCRγδ, Vα24, CD3, CD8α, CD95, CD62L, CD161 and IL-18Rα for 20 minutes on ice. After washing in ice cold FACS buffer, samples were analyzed on a BD FacsARIA flow cytometer.

CM and EM subsets were identified as CD62L$^+$ or CD62L$^-$ events, respectively, in the CD4$^-$/CD16$^-$/TCRγδ$^-$/Vα24$^-$/CD3$^+$/CD8$^+$/CD95$^+$ population. Rh123 fluorescence was identified with appropriate compensation and a 530/30 emission filter after laser excitation at 488 nm. Rh123-effluxing events were defined as those with fluorescence lower than the mean fluorescence intensity identified after culture in the presence of vinblastine efflux blockade.

The results in FIG. 1 demonstrate that many lymphocytes have the capacity to efflux Rh123; however only small subsets of CM and EM CD8$^+$ T lymphocytes have the capacity to rapidly efflux Rh123 over a 30 minute period. Efflux is blocked by vinblastine, a non-fluorescent substrate for MDR-1 and MRP-1, demonstrating specificity of Rh123 efflux. CM and EM cells rapidly effluxing Rh123 express high levels of IL-18Rα and CD161.

Example 2

CMhi and EMhi Subsets are TCRαβ$^+$ and TCRγδ$^-$. There is No Restriction to Vα24. They are Predominantly CD45RA$^{int/neg}$, CD45RO$^{int/hi}$, CD95$^+$, CD8α$^+$, CD8β$^{+/neg}$, CD25$^{neg}$, CD27$^+$, CD56$^{pos/neg}$, CD57$^{neg}$, CD28$^{hi}$, CD122$^+$, CD127$^{hi}$, PD-1$^{neg}$, CD103$^{neg}$, NKG2D$^{int/lo}$, perforin$^{lo/int}$, granzyme A$^{int}$, granzyme B$^{neg}$, Ki67$^{neg}$, bcl-xL$^{hi}$ and bcl-2$^{hi}$.

PBMC were separated from fresh peripheral blood by density gradient centrifugation and resuspended in PBS. Surface labeling was performed with antibodies to CD4, CD16, TCRγδ, Vα24, CD3, CD8α, CD95, CD62L, CD161 and other antibodies as indicated for 20 minutes on ice. After washing in cold PBS, surface-labeled samples were analyzed on a BD LSR-2 flow cytometer. Samples for intracellular staining were fixed in BD Cytofix before washing, permeabilization and labeling in BD Perm/wash buffer, then analyzed as above.

CMhi and EMhi subsets were identified as CD62L$^+$/CD161$^{hi}$ or CD62L$^-$/161$^{hi}$ events, respectively, in the CD4$^-$/CD16$^-$/TCRγδ$^-$/Vα24$^-$/CD3$^+$/CD8$^+$ and CD95$^+$ populations.

Figure 2A:
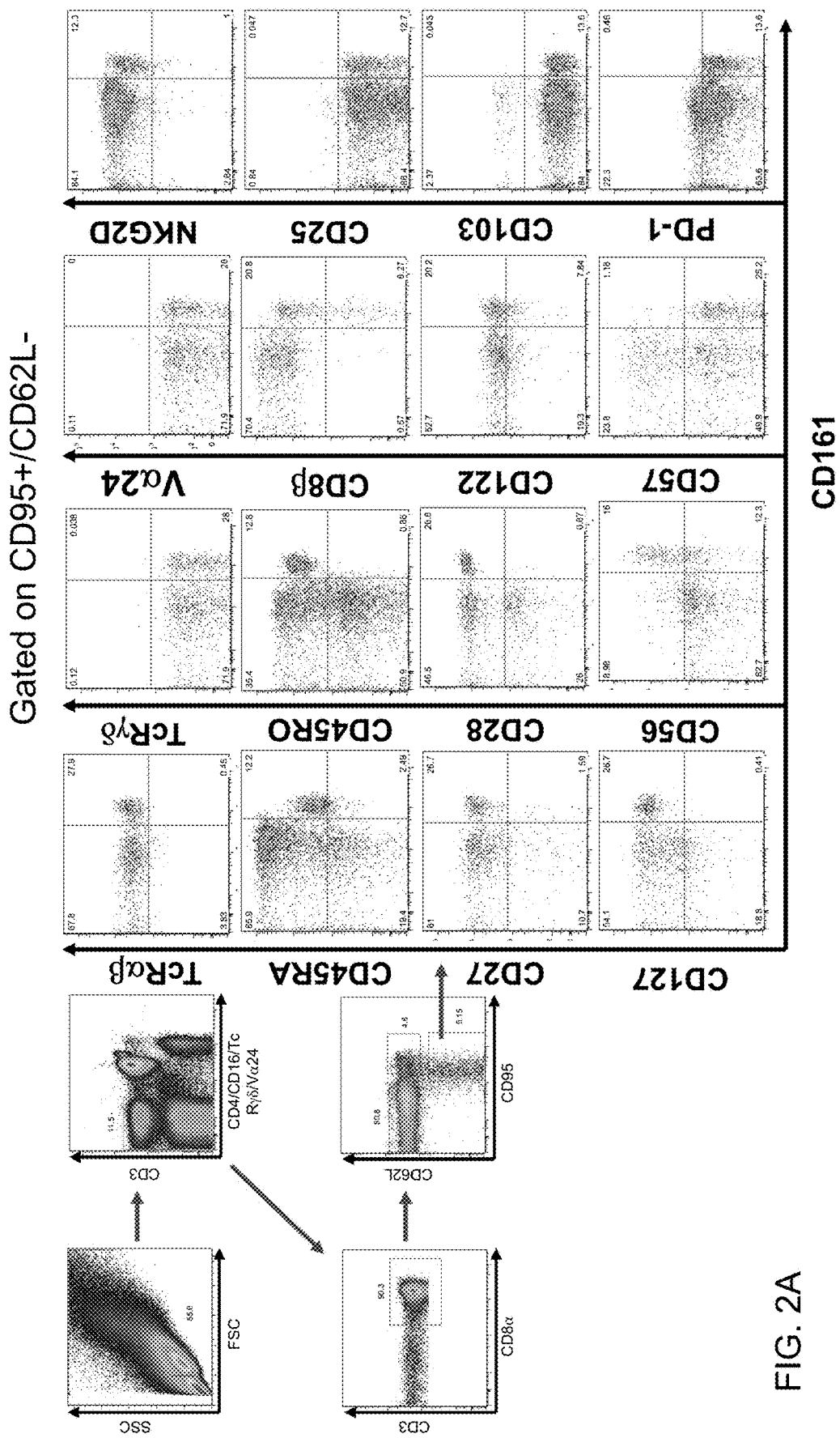
FIGS. 2A-2C: CMhi and EMhi subsets are TCRαβ+ and TCRγδ−. There is no restriction to Vα24. They are predominantly CD45RA$^{int/neg}$, CD45RO$^{int/hi}$, CD95+, CD8α+, CD8β$^{+/neg}$, CD27+, CD28+, CD122+, perforin$^{int/lo}$, granzyme A$^{int/lo}$, granzyme B$^{neg}$, Ki67$^{neg}$, bcl-xL$^{int/hi}$ and bcl-2$^{int/hi}$, as described in Example 2.
Figure 2B:
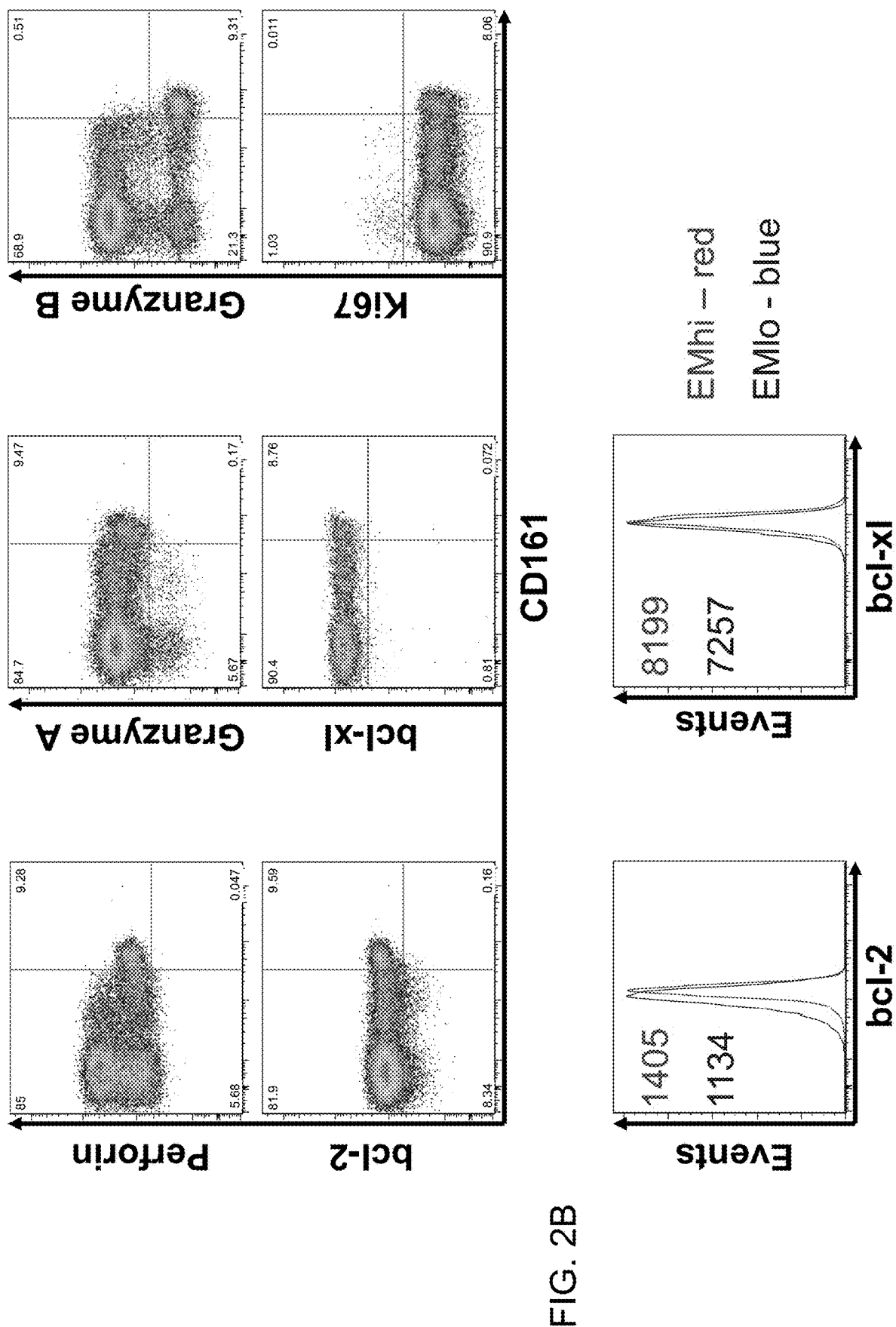
Figure 2C:
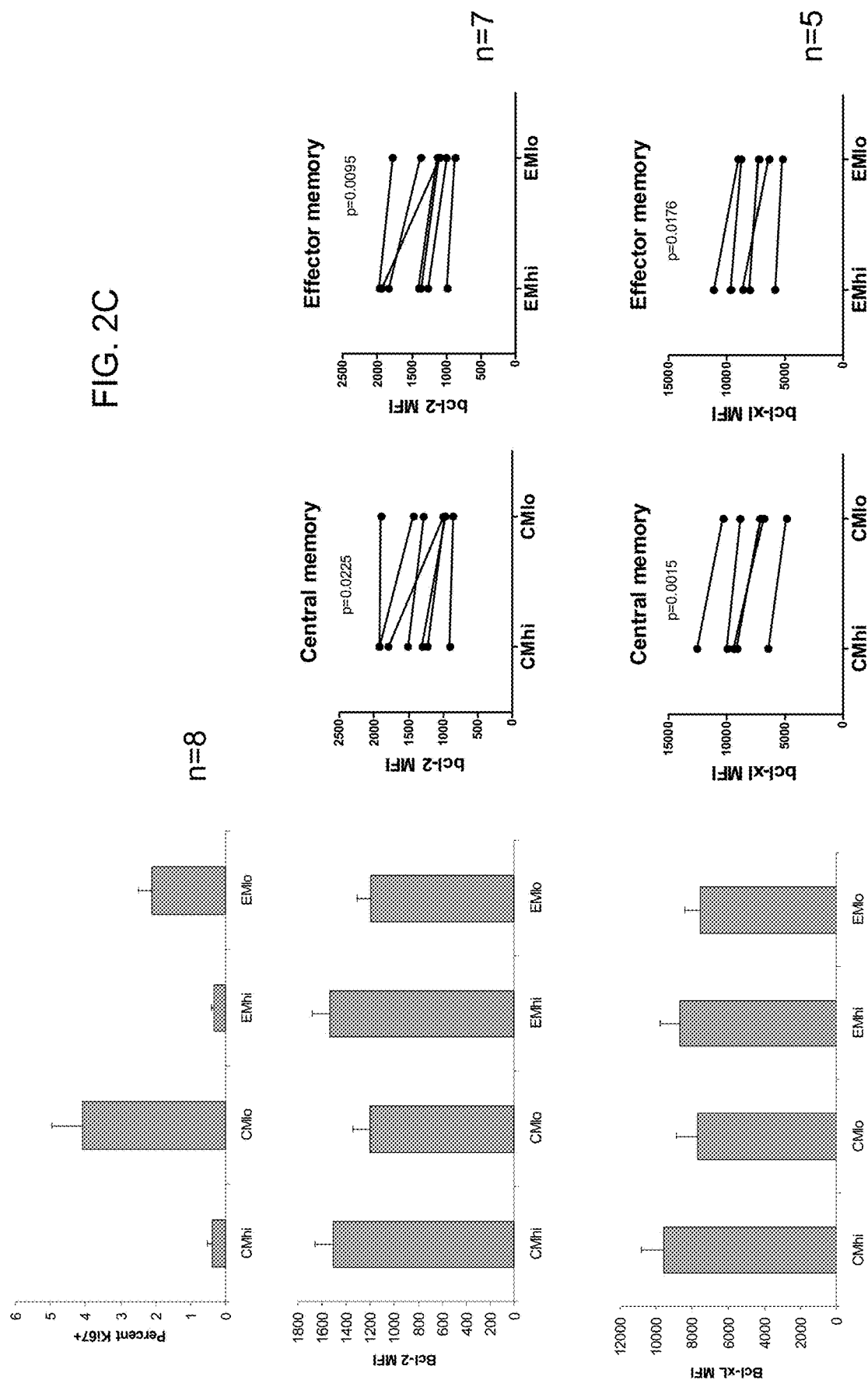

The results in FIGS. 2a-c) demonstrate the unique phenotype of CMhi and EMhi subsets of CD8$^+$ TCRαβ$^+$ T cells. The phenotype is consistent with a memory population and is similar to murine memory stem cells as described by Zhang et al (Nat Med, 2005). The phenotype is different from that expected for other characterized lymphoid populations, such as NK cells and invariant NKT cells. CMhi and EMhi have a similar phenotype, but can be immunophenotypically differentiated by the expression of CD62L. Only the phenotype of EMhi is shown for clarity in FIGS. 2a) and b). FIG. 2c) is shown to illustrate the higher expression of bcl-2 and bcl-xl and lower expression of Ki67 in CMhi and EMhi, compared to CMlo and EMlo, from all donors tested.

Example 3

CMhi and EMhi Have a Surface Phenotype That Suggests Derivation from the Distal Pole of an Asymmetrically Dividing CD8$^+$ T Cell or Uropod of a Polarized CD8$^+$ T Cell PBMC were separated from fresh peripheral blood by density gradient centrifugation, washed in efflux buffer and resuspended at 1×10$^6$/ml in ice cold efflux buffer with 5 µg/ml rhodamine 123. PBMC were incubated for 30 minutes on ice before washing three times in ice cold efflux buffer and resuspending in pre-warmed efflux buffer for 30 minutes at 37° C. At 30 minutes, PBMC were washed once in ice cold PBS/0.2% BSA (FACS buffer) and labeled with antibodies to CD3, CD4, CD8, CD45RA, CD45RO, CD62L, CD16 and either CD11a, CD43, CD44, CD46, CD148 or CD162 for 20 minutes on ice. After washing in ice cold FACS buffer, samples were analyzed on a BD FacsARIA flow cytometry. CM and EM subsets were identified as CD62L$^+$ or CD62L$^-$ events, respectively, in the CD4$^-$/CD16$^-$/CD3$^+$/CD8$^+$/CD45RA$^{int/neg}$/CD45RO$^+$ population. Establishment of rapid efflux was performed as described in Example 1.

Figure 3:
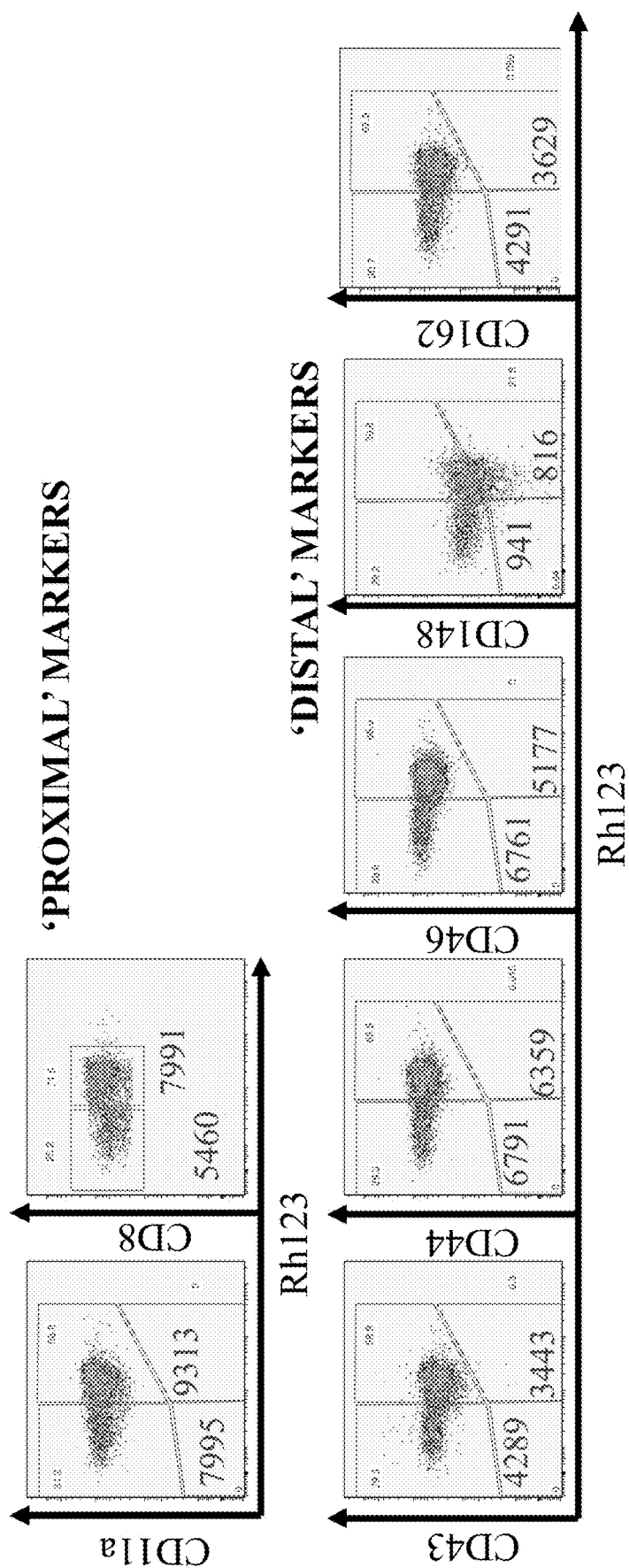
FIG. 3: CMhi and EMhi have a surface phenotype that suggests possible derivation from the distal pole of an asymmetrically dividing naïve CD8+ T cell, as described in Example 3.

FIG. 3 indicates that CMhi have a phenotype consistent with derivation from the 'memory' distal pole of a dividing CD8$^+$ T cell or uropod of a polarized CD8+ T cell. The phenotype of CMhi is similar to the phenotype of EMhi—only FACS profiles gated on CM CD8$^+$ T cells are shown for clarity. The MFIs of CMhi and CMlo populations are shown in red. After TCR signaling in the presence of appropriate costimulation and/or adhesion molecules, an immune synapse forms between the APC and T cell. CD8 and CD11 a (amongst other cell surface proteins) actively localize to the immune synapse ("Proximal markers") and CD43, CD44, CD46, CD148 and CD162 are excluded from the synapse and form the distal pole complex ("Distal markers"). A similar structure to the distal pole complex, the uropod, is also formed on stimulation of some T cells with chemokines and has a similar pattern of expression of cell surface markers. It is unknown whether these surface molecules remain localized within or outside the immune synapse or uropod until or beyond the first cell division; however the phenotype of CMhi and EMhi, while variable, could be consistent with cell populations that are derived from the distal pole of a dividing memory cell or the uropod.

Example 4

Figures 4A, 4B:
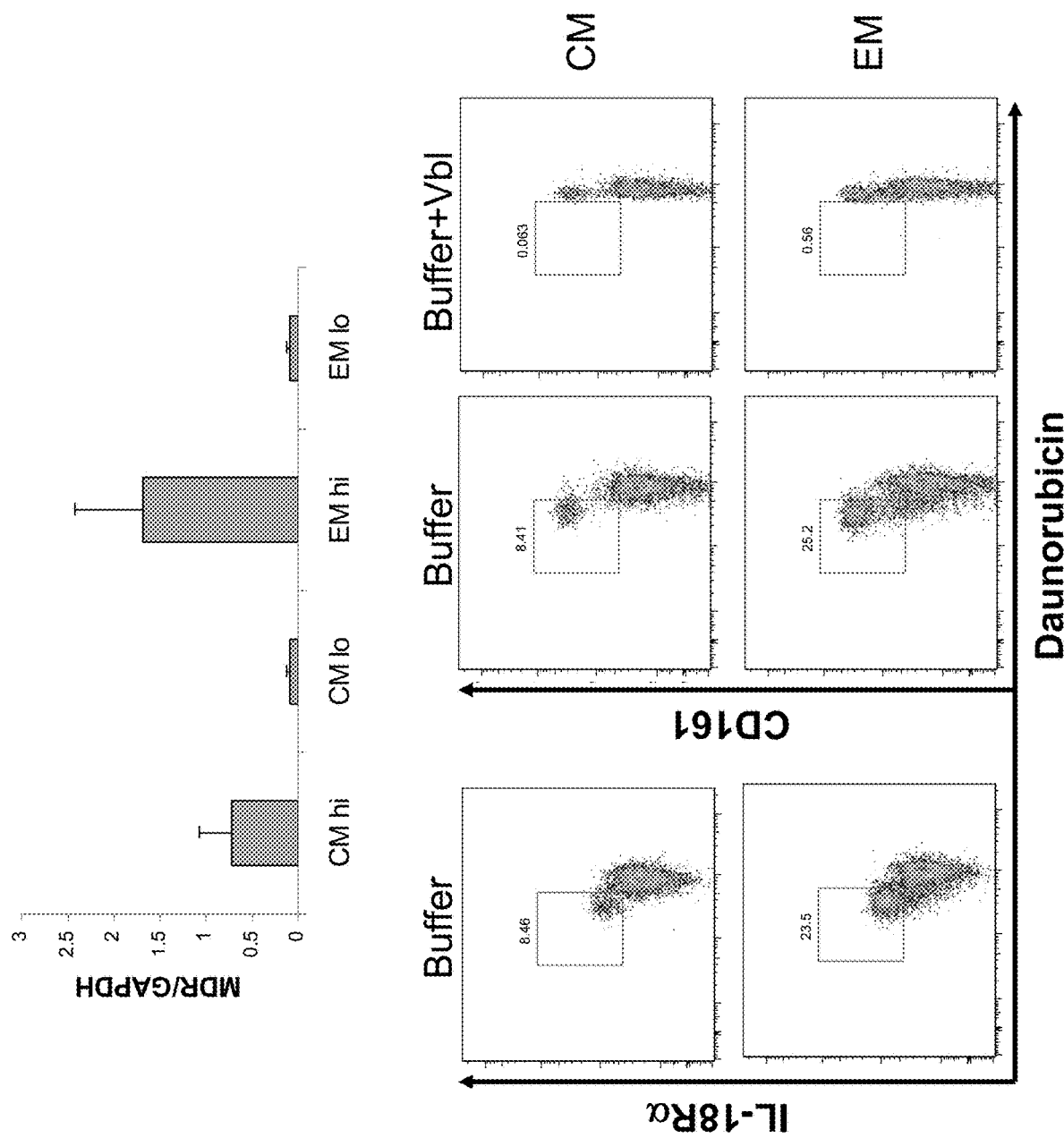
FIGS. 4A-4B: CMhi and EMhi express higher levels of MDR-1 mRNA than their non-effluxing counterparts and actively efflux the fluorescent chemotherapy drug, daunorubicin, as described in Example 4.

CMhi and EMhi Express Higher Levels of MDR-1 mRNA Than Their Non-effluxing Counterparts and Actively Efflux the Fluorescent Chemotherapy Drug, Daunorubicin In FIG. 4(a), CMhi and EMhi and their non-effluxing IL-18Rα$^{lo/neg}$ counterparts (CMlo and EMlo) were isolated using negative immunomagnetic selection of CD8$^+$ T cells with biotinylated antibodies to non-CD8$^+$ T cells, followed by surface labeling with fluorochrome-conjugated streptavidin to identify non-CD8$^+$ T cells, CD95, CD62L and IL-18Rα and sorting on a BD FacsARIA flow sorter. CM and EM CD8$^+$ T cells were defined as streptavidin$^-$/CD95$^+$/CD62L$^+$ or streptavidin$^-$/CD95$^+$/CD62L$^-$, respectively. CMhi and EMhi were defined by high expression of IL-18Rα. Expression of mdr 1 in isolated CMhi, CMlo, EMhi and EMlo subsets was determined by quantitative polymerase chain reaction, using the following primers and probes: MDR1 forward—GGA AGC CAA TGC CTA TGA CTT TA; MDR1 reverse—GAA CCA CTG CTT CGC TTT CTG; MDR1 probe—6FAM-TGA AAC TGC CTC ATA AAT TTG ACA CCC TGG-TAMRA. Results shown are normalized to GAPDH expression. The mean/SE from 3 normal donors are shown.

In FIG. 4(b), PBMC were resuspended at 1×10$^6$/ml in efflux buffer and loaded with the fluorescent chemotherapy drug, daunorubicin, at 2.5 µM for 20 minutes at 37° C., before washing three times and effluxing with or without vinblastine 25 μM for 1 hour at 37° C. PBMC were then washed once in ice cold PBS/0.2% BSA (FACS buffer) and labeled with antibodies to CD16, CD3, CD8α, CD95, CD62L and CD161 or IL-18Rα for 20 minutes on ice. After washing in ice cold FACS buffer, samples were analyzed on a BD LSR-2 flow cytometer.

The data indicate that CMhi and EMhi express high levels of mRNA for MDR-1, the ATP-binding cassette (ABC) co-transporter responsible for specific and active efflux of Rh123 and daunorubicin. The capacity of CMhi and EMhi (defined by either high IL-18Rα or CD161 expression) to actively and specifically efflux a chemotherapy drug is shown by the inhibition of efflux in the presence of a competitive agonist for MDR-1 protein, vinblastine. Inhibition was also achieved with two other MDR-1 channel blockers, PK11195 and cyclosporine A (data not shown).

Example 5

CMhi and EMhi are Resistant to Daunorubicin-Induced Apoptosis In Vitro

CMhi and EMhi and their non-effluxing IL-18Rα$^{lo/neg}$ counterparts (CMlo and EMlo) were isolated using negative immunomagnetic selection of CD8$^+$ T cells with biotinylated antibodies to non-CD8$^+$ T cells, followed by surface labeling with fluorochrome-conjugated streptavidin to identify non-CD8$^+$ T cells, CD95, CD62L and IL-18Rα and sorting on a BD FacsARIA flow sorter. CM and EM CD8$^+$ T cells were defined as streptavidin$^-$/CD95$^+$/CD62L$^+$ or streptavidin$^-$/CD95$^+$/CD62L$^-$, respectively. CMhi and EMhi were defined by high expression of IL-18Rα. Effluxing and non-effluxing CM and EM subsets were cultured for 44 hours in the presence or absence of daunorubicin (an anthracycline chemotherapeutic agent, effluxed by the ABC-B1 cotransporter, MDR-1), with or without MDR-1 blockade with the peripheral benzodiazepine receptor antagonist, PK11195. Cultures were harvested, washed twice with cold PBS and stained with Annexin V and DAPI before analysis.

Figure 5:
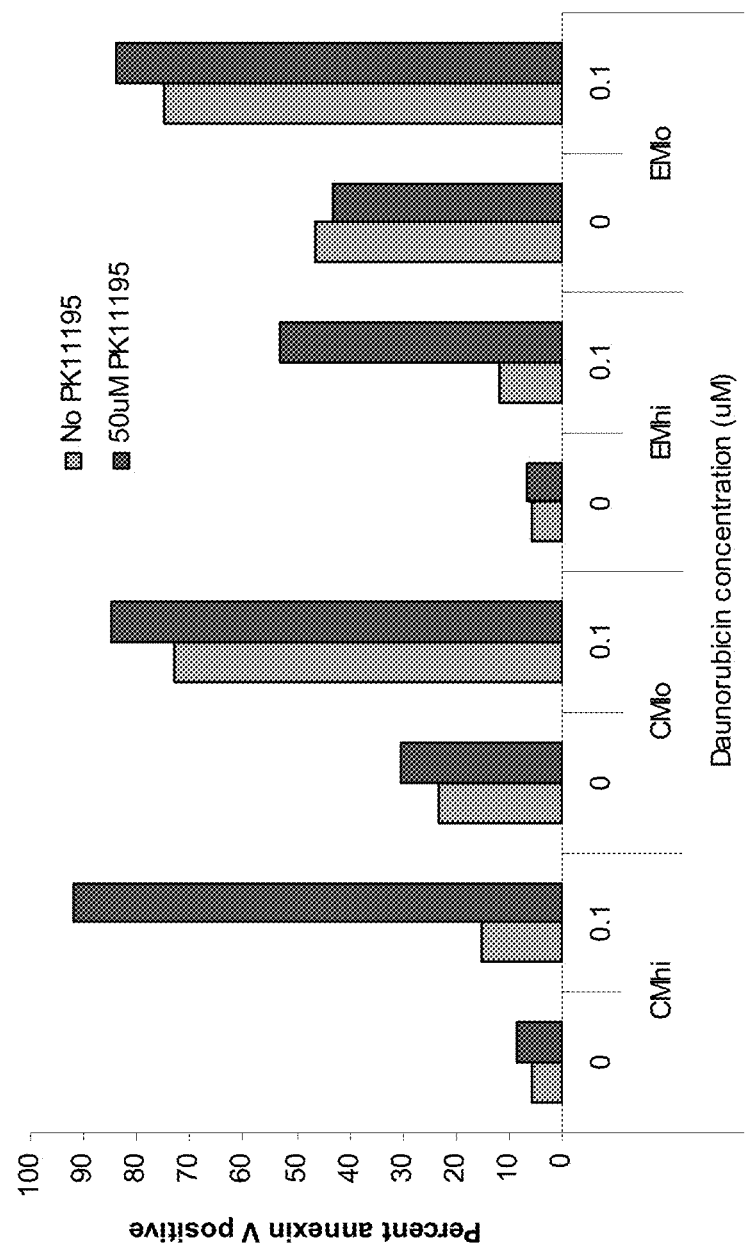
FIG. 5: CMhi and EMhi are resistant to daunorubicin-induced apoptosis in vitro, as described in Example 5.

The results in FIG. 5 indicate that CMhi and EMhi subsets are resistant to apoptosis induced by culture with daunorubicin at pharmacological concentrations (0.1 uM). Chemoresistance is mediated by efflux pumps as inhibition of MDR-1 with PK11195 results in increased cell death. Culture with PK11195 alone does not impair viability.

Example 6

CMhi and EMhi Divide in Response to the Homeostatic Cytokines, IL-7 and IL-15, and Have High Viability After Culture in the Absence of Supplementary Cytokines In FIGS. 6(a-c), PBMC were separated from fresh peripheral blood by density gradient centrifugation. CD8$^+$ T cells were positively selected using CD8 Microbeads (Miltenyi) and resuspended at 1×10$^6$/ml in ice cold efflux buffer with 10 μg/ml Rh123. CD8$^+$ T cells were incubated for 30 minutes on ice before washing three times in ice cold efflux buffer and resuspending in pre-warmed efflux buffer for 30 minutes at 37° C. Vinblastine was added to control samples to establish the presence of efflux). CD8$^+$ T cells were then washed once in ice cold PBS/0.2% BSA (FACS buffer) and labeled with fluorochrome-conjugated antibodies to CD4, CD16, TCRγδ, Vα24, CD8α, CD95, CD62L and CD161. CMhi and EMhi subsets were identified as CD62L$^+$/Rh123$^{lo}$/CD161$^{hi}$ or CD62L$^-$/Rh123$^{lo}$/CD161$^{hi}$ events, respectively, in the CD4$^-$/CD16$^-$/TCRγδ$^-$/Vα24$^-$/CD8$^+$ population. CMlo and EMlo subsets were identified as CD62L$^+$/Rh123$^{hi}$/CD161$^{int/neg}$ or CD62L$^-$/Rh123$^{hi}$/CD161$^{int/neg}$ events, respectively, in the CD4$^-$/CD16$^-$/TCRγδ$^-$/Vα24$^-$/CD8$^+$/CD95$^+$ population. The gating strategy is shown in FIG. 6a). Subsets were isolated using a BD FacsARIA flow sorter and proliferation in response to IL-7 was determined by $^3$H-thymidine uptake or CFSE dilution assays. Proliferation in response to IL-15 was determined by CFSE dilution assay. The $^3$H-thymidine proliferation assay was performed by culturing for 5 days in CTL medium supplemented with IL-7 then pulsing overnight with $^3$H-thymidine before harvesting and counting. The CFSE-dilution assay was performed by loading the cells with CFSE and culturing for 10 days, before viability labeling with DAPI and analysis on a BD LSR2 flow cytometer.

Figure 6A:
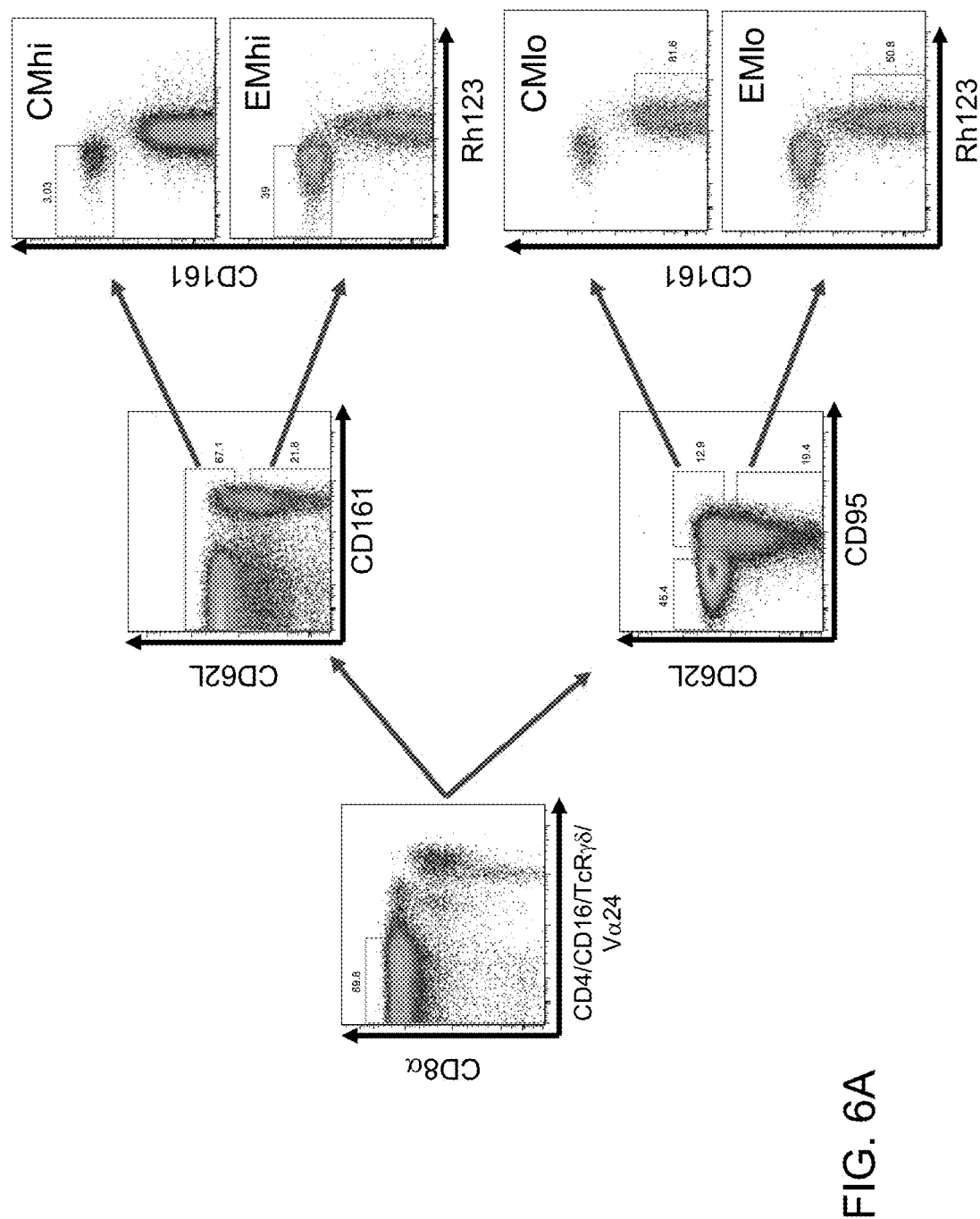
FIGS. 6A-6D: CMhi and EMhi divide in response to the homeostatic cytokines, IL-7 and IL-15, and have high viability after culture in the absence of supplementary cytokines, as described in Example 6.
Figure 6B:
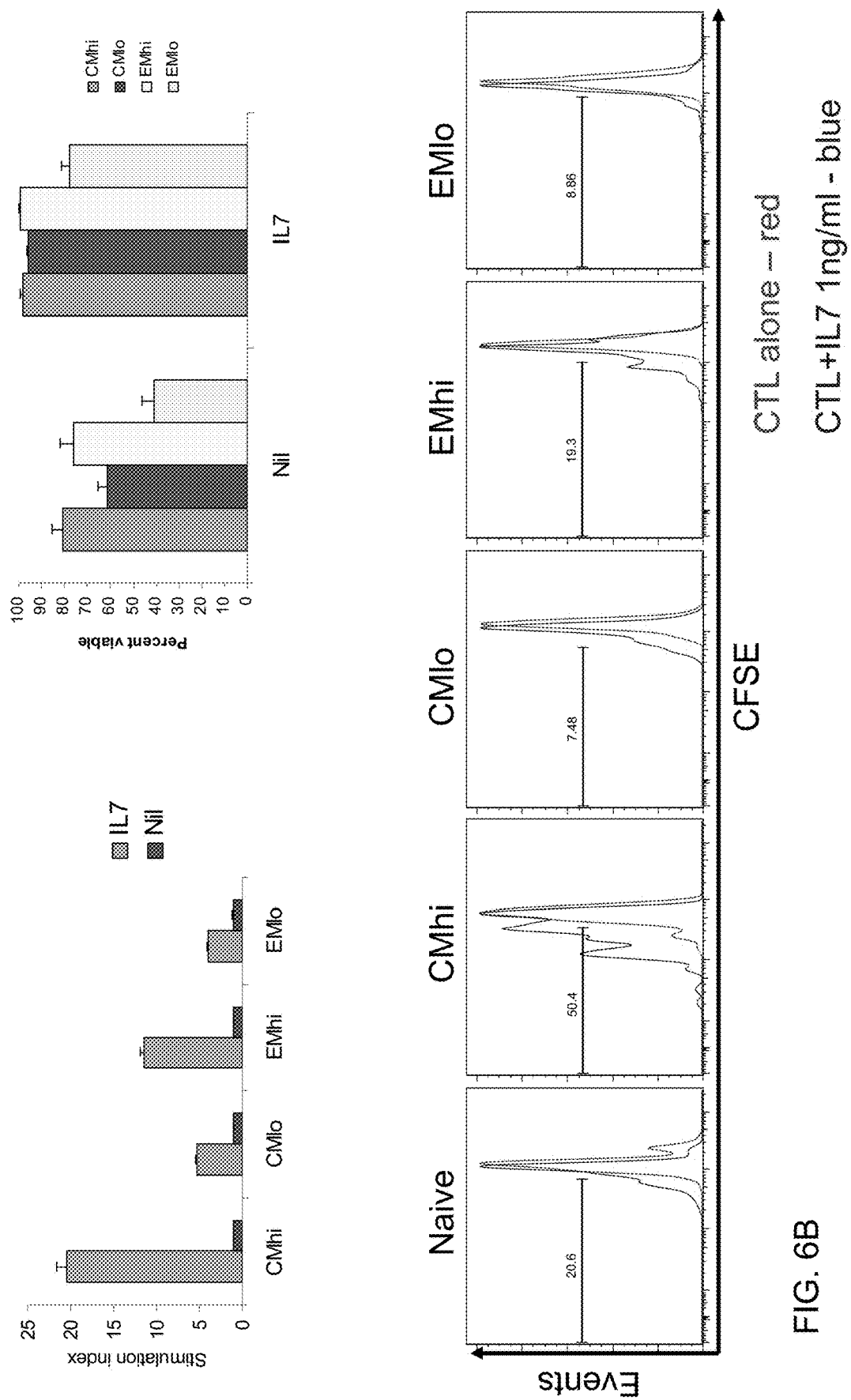
Figure 6C:
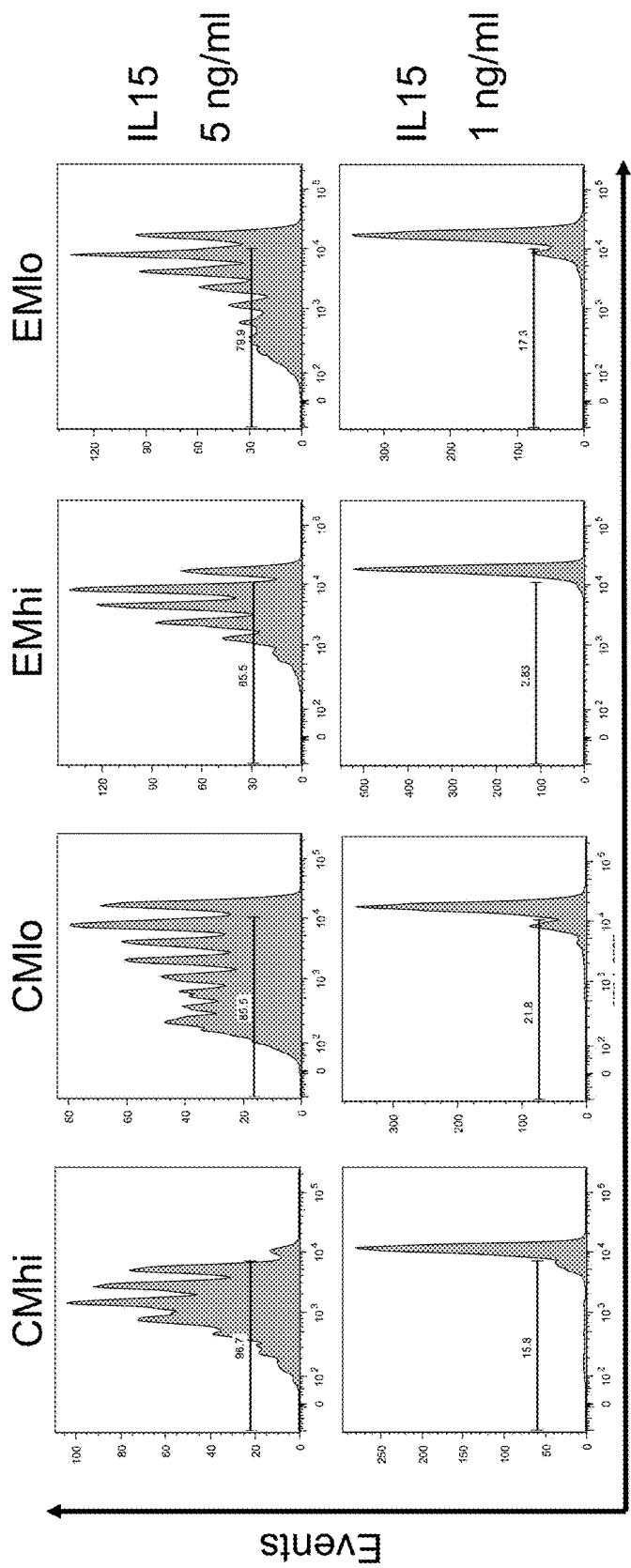
Figure 6D:
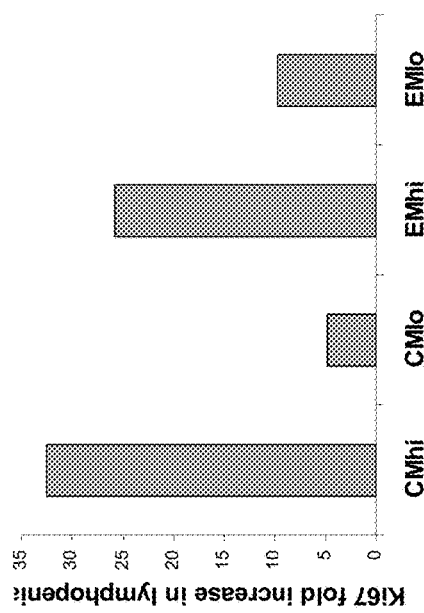

In FIG. 6(d), PBMC from non-lymphopenic healthy donors (n=8) or lymphopenic acute myeloid leukemia patients (n=6) at the nadir (day 11 to day 22) of induction therapy were analyzed for Ki67 expression on memory subsets as described in Example 2. The fold change in the percent Ki67 expression of CD8$^+$ T cell subsets between non-lymphopenic healthy donors and lymphopenic patients is depicted.

The results indicate that the CMhi and EMhi subsets have the capacity to enter the cell cycle and undergo division in response to IL-7 (FIG. 6b) and IL-15 (FIG. 6c) stimulation. CMhi and EMhi are also recruited more effectively into the cell cycle than CMlo and EMlo in lymphopenic chemotherapy patients (FIG. 6d), suggesting high sensitivity to lymphopenia-induced IL-7 and IL-15-mediated proliferation. In addition, CMhi and EMhi maintain higher viability in culture in the absence of supplementary cytokines than their non-effluxing counterparts (FIG. 6b). IL-7 and IL-15 are critical for the maintenance of long term memory and survival of memory T cells and the CMhi and EMhi subsets are sensitive to signaling by IL-7 and IL-15.

Example 7

Figure 7:
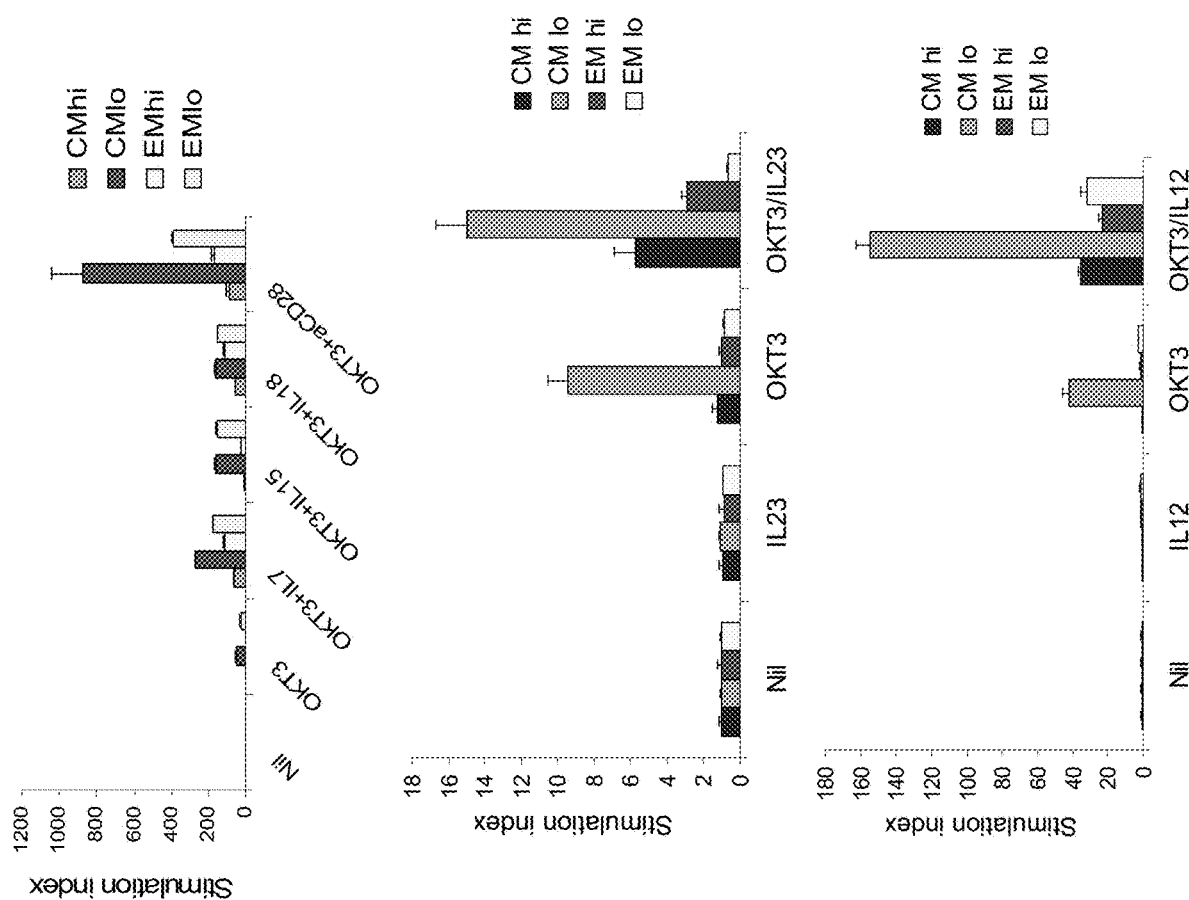
FIG. 7: CMhi and EMhi show reduced $^3$H-thymidine uptake in response to polyclonal TCR stimulation with OKT3, compared to their non-effluxing counterparts, as described in Example 7. $^3$H-thymidine uptake is increased after costimulation as indicated in the Figure.
Figure 8:
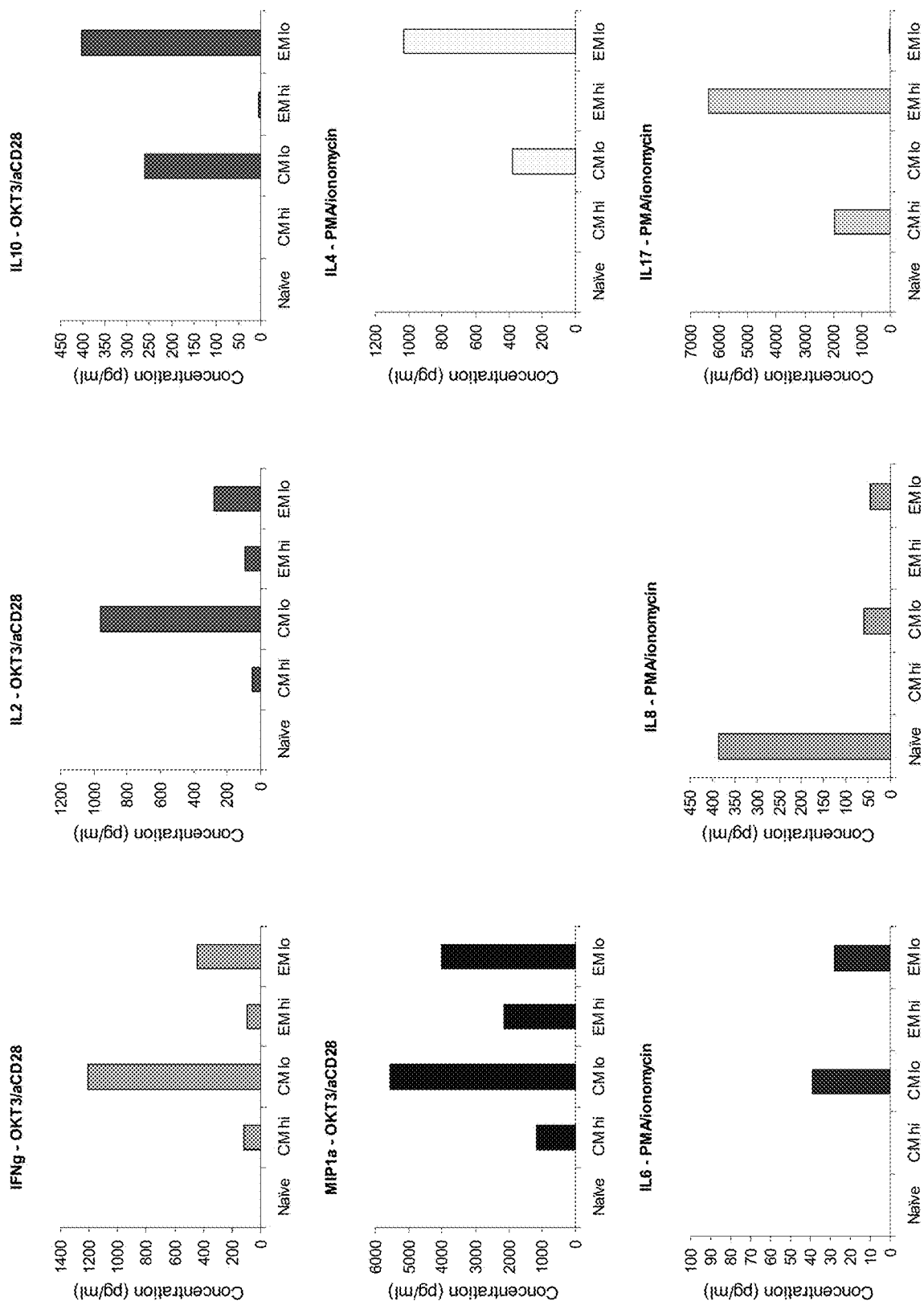
FIG. 8: CMhi and EMhi have a different cytokine secretion profile compared to their non-effluxing counterparts, as described in Example 8.
Figure 9:
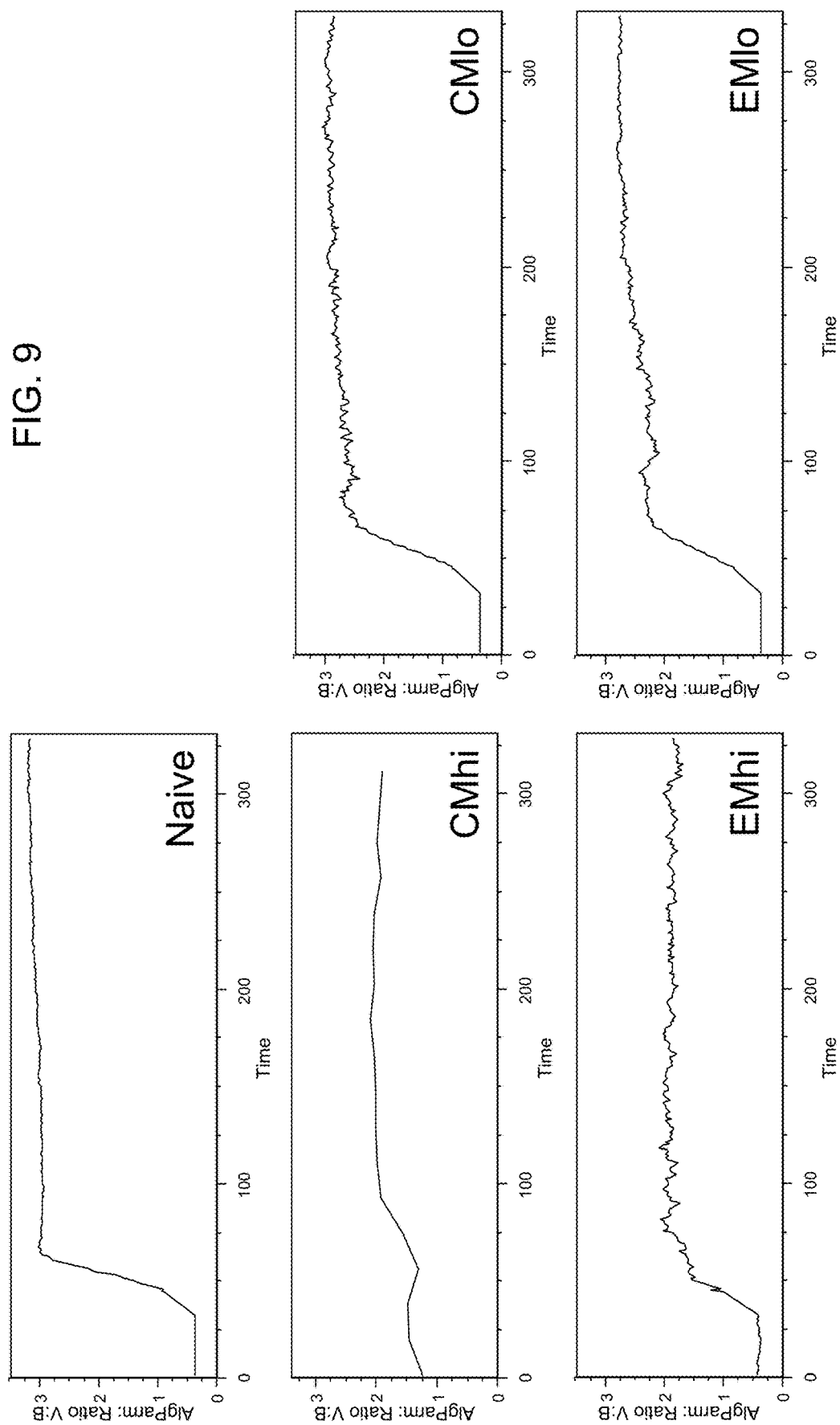
FIG. 9: CMhi and EMhi have decreased calcium flux in response to ionomycin, compared to their non-effluxing counterparts, as described in Example 9.
Figure 10:
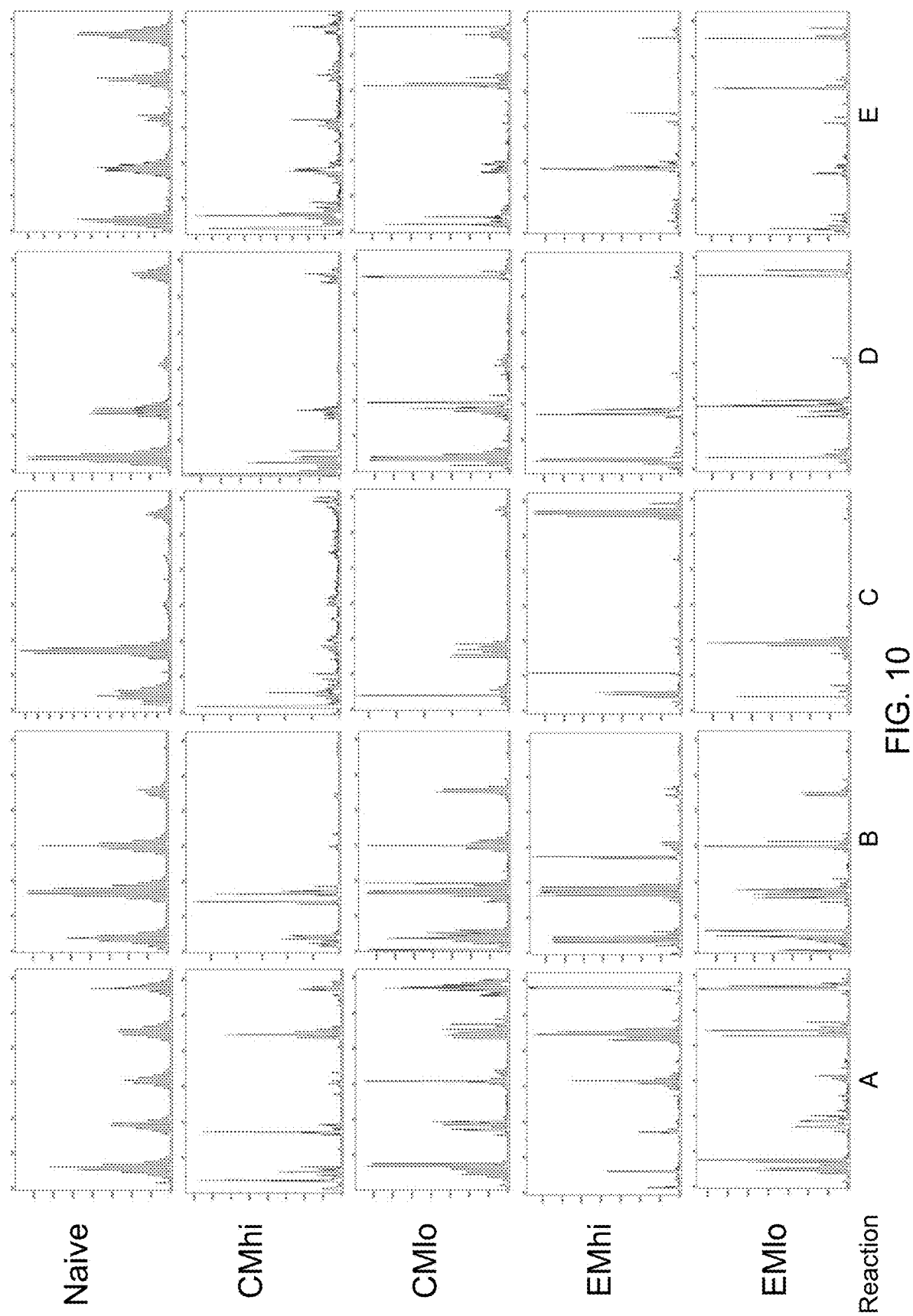
FIG. 10: CMhi and EMhi subsets comprise polyclonal TCR repertoires by molecular spectratyping, as described in Example 10.

CMhi and EMhi Show Reduced $^3$H-thymidine Uptake, Compared to Their Non-effluxing Counterparts, in Response to Polyclonal TCR Stimulation with OKT3, and Can be Rescued After Costimulation as Indicated in FIG. 7

CMhi, CMlo, EMhi and EMlo were isolated as described in Example 6. PBMC were separated from fresh peripheral blood by density gradient centrifugation. CD8$^+$ T cells were positively selected using CD8 paramagnetic beads and resuspended at 1×10$^6$/ml in ice cold efflux buffer with 10 μg/ml Rh123. CD8$^+$ T cells were incubated for 30 minutes on ice before washing three times in ice cold efflux buffer and resuspending in pre-warmed efflux buffer, with or without vinblastine, for 30 minutes at 37° C. At 30 minutes, CD8$^+$ T cells were washed once in ice cold PBS/0.2% BSA (FACS buffer) and labeled with fluorochrome-conjugated antibodies to CD4, CD16, TCRγδ, Vα24, CD8α, CD95, CD62L and CD161. CMhi and EMhi subsets were identified as CD62L$^+$/Rh123$^{lo}$/CD161$^{hi}$ or CD62L$^-$/Rh123$^{lo}$/CD161$^{hi}$ events, respectively, in the CD4$^-$/CD16$^-$/TCRγδ$^-$/Vα24$^-$/CD8$^+$ population. CMlo and EMlo subsets were identified as CD62L$^+$/Rh123$^{hi}$/CD161$^{int/neg}$ or CD62L$^-$/Rh123$^{hi}$/CD161$^{int/neg}$ events, respectively, in the CD4$^-$/CD16$^-$/TCRγδ$^-$/Vα24$^-$/CD8$^+$/CD95$^+$ population. Subsets were isolated using a BD FacsARIA flow sorter and cultured in 96 well plates at 10,000-30,000 per well in 200 µl CTL in the indicated conditions. OKT3 was plate-bound by incubating at 1000 ng/ml in 100 µl PBS per well for 6 hours at 4° C., then washing twice with 200 ul cold PBS before plating the sorted subsets. Anti-CD28 was plate-bound (at 5 µg/ml) with OKT3, as above. Cytokine concentrations were as follows: IL-7, 2 ng/ml; IL12, 10 ng/ml; IL-15, 1 ng/ml, IL-18, 80 ng/ml; IL-23, 10 ng/ml. Culture with cytokines in the absence of cytokine costimulation resulted in minimal proliferation. Data for the proliferation of the CMhi subset with IL-12 alone or OKT3/IL-12 is not available.

Example 8

CMhi and EMhi Have a Different Cytokine Secretion Profile Compared to Their Non-effluxing Counterparts CMhi, CMlo, EMhi and EMlo were isolated as described in Example 6. PBMC were separated from fresh peripheral blood by density gradient centrifugation. $CD8^+$ T cells were positively selected using CD8 paramagnetic beads and resuspended at $1\times10^6$/ml in ice cold efflux buffer with 10 µg/ml Rh123. $CD8^+$ T cells were incubated for 30 minutes on ice before washing three times in ice cold efflux buffer and resuspending in pre-warmed efflux buffer, with or without vinblastine, for 30 minutes at 37° C. At 30 minutes, $CD8^+$ T cells were washed once in ice cold PBS/0.2% BSA (FACS buffer) and labeled with fluorochrome-conjugated antibodies to CD4, CD16, TCRγδ, Vα24, CD8α, CD95, CD62L and CD161. CMhi and EMhi subsets were identified as $CD62L^+/Rh123^{lo}/CD161^{hi}$ or $CD62L^-/Rh123^{lo}/CD161^{hi}$ events, respectively, in the $CD4^-/CD16^-/TCRγδ^-/Vα24^-/CD8^+$ population. CMlo and EMlo subsets were identified as $CD62L^+/Rh123^{hi}/CD161^{int/neg}$ or $CD62L^-/Rh123^{hi}/CD161^{int/neg}$ events, respectively, in the $CD4^-/CD16^-/TCRγδ^-/Vα24^-/CD8^+/CD95^+$ population. Subsets were isolated using a BD FacsARIA flow sorter and plated in 200 µl CTL medium at 60,000 cells per well. Polyclonal stimulation was performed by culturing isolated subsets with either PMA (5 ng/ml)/ionomycin (1 µg/ml) or plate-bound OKT3/anti-CD28 (prepared as described in Example 7) for 20 hours. Cytokine secretion was detected in culture supernatant using a Luminex Cytokine Array assay.

These experiments show that CMhi and EMhi secrete less IL-2, IL-4, IL-6, IL-8, IL-10, IFN-γ and MIP-1α and more IL-17 than their non-effluxing counterparts in response to polyclonal stimulation.

Example 9

CMhi and EMhi Have Decreased Calcium Flux in Response to Ionomycin, Compared to Their Non-effluxing Counterparts PBMC were separated from fresh peripheral blood by density gradient centrifugation at room temperature and incubated at $1\times10^7$/ml in CTL medium supplemented with Indo-1AM (Sigma) 10 µM and probenicid 4 mM for 30 minutes at 37° C. The PBMC were washed once in CTL medium at 25° C. Surface labeling was performed in CTL medium with antibodies to CD4, CD16, TCRγδ, Vα24, CD8α, CD62L and CD161 for 10 minutes at room temperature. After washing in room temperature CTL medium, surface-labeled samples were warmed to 37° C. for 4 minutes before high speed acquisition on a BD LSR-2 flow cytometer equipped with UV, violet, blue, green and red lasers. After 30 seconds acquisition, the sample was removed from the aspiration port, ionomycin was added to a final concentration of 5 µg/ml, the sample was returned and acquisition was continued at 20,000 events/second. CMhi and EMhi subsets were identified as $CD62L^+/CD161^{hi}$ or $CD62L^-/CD161^{hi}$ events, respectively, in the $CD4^-/CD16^-/TCRγδ^-/Vα24^-/CD8^+/CD95^+$ populations. CMlo and EMlo subsets were identified as $CD62L^+/CD161^{int/neg}$ or $CD62L^-/CD161^{int/neg}$ events, respectively, in the $CD4^-/CD16^-/TCRγδ^-/Vα24^-/CD8^+/CD95^+$ populations. Relative intracellular calcium concentration was measured as the ratio of Indo-1AM fluorescence in the UV violet (405 nm):UV blue (505 nm) detectors and is plotted as the mean ratio versus time (seconds) for appropriately gated subsets.

This experiment demonstrates that CMhi and EMhi subsets have a different capacity to flux calcium in response to the calcium ionophore, ionomycin, compared to their non-effluxing counterparts. Calcium flux is a proximal signaling event downstream from antigen-specific TCR ligation.

Example 10

CMhi and EMhi Subsets Comprise Polyclonal TCR Repertoires by Molecular Spectratyping, as Described in Example 10

CMhi, CMlo, EMhi and EMlo were isolated as described in Example 6. PBMC were separated from fresh peripheral blood by density gradient centrifugation. $CD8^+$ T cells were positively selected using CD8 paramagnetic beads and resuspended at $1\times10^6$/ml in ice cold efflux buffer with 10 µg/ml Rh123. $CD8^+$ T cells were incubated for 30 minutes on ice before washing three times in ice cold efflux buffer and resuspending in pre-warmed efflux buffer, with or without vinblastine, for 30 minutes at 37° C. At 30 minutes, $CD8^+$ T cells were washed once in ice cold PBS/0.2% BSA (FACS buffer) and labeled with fluorochrome-conjugated antibodies to CD4, CD16, TCRγδ, Vα24, CD8α, CD95, CD62L and CD161. CMhi and EMhi subsets were identified as $CD62L^+/Rh123^{lo}/CD161^{hi}$ or $CD62L^-/Rh123^{lo}/CD161^{hi}$ events, respectively, in the $CD4^-/CD16^-/TCRγδ^-/Vα24^-/CD8^+$ population. CMlo and EMlo subsets were identified as $CD62L^+/Rh123^{hi}/CD161^{int/neg}$ or $CD62L^-/Rh123^{hi}/CD161^{int/neg}$ events, respectively, in the $CD4^-/CD16^-/TCRγδ^-/Vα24^-/CD8^+/CD95^+$ population. Naïve $CD8^+$ T cells were identified as $CD4^-/CD16^-/TCRγδ^-/Vα24^-/CD8^+/CD95^-/CD62L^+$ events. Subsets were isolated using a BD FacsARIA flow sorter.

Molecular Vβ spectratyping was performed on isolated subsets and naïve $CD8^+$ T cells by multiplex RT-PCR and Genescan analysis of TCR Vβ fragments.

These experiments show polyclonal TCR Vβ usage in the effluxing CMhi and EMhi subsets, demonstrating that the $CD8^+$ T cells within the CMhi and EMhi subsets express diverse TCR that are potentially specific for a broad range of antigens.

Example 11

Viral Antigen Tetramer-Positive Cells Can be Identified within CMhi and EMhi Subsets and CMV-, EBV- and Influenza-Specific CTL Responses Can be Generated from Sorted CMhi and EMhi Subsets, as Described in Example 11

PBMC were separated from fresh peripheral blood by density gradient centrifugation and resuspended in PBS.

Figure 11A:
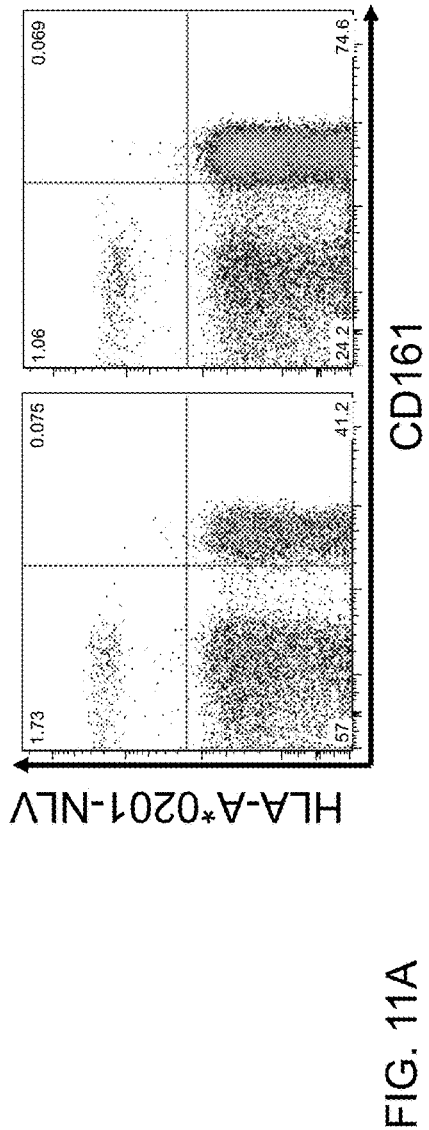
FIGS. 11A-11B: Viral antigen tetramer-positive cells can be identified within CMhi and EMhi subsets and CMV-, EBV- and influenza-specific CTL responses can be generated from sorted CMhi and EMhi subsets, as described in Example 11.

Surface labeling was performed with antibodies to CD4, CD16, TCRγδ, CD8α, CD95, CD62L, CD161 and an APC-labeled HLA-A*0201; NLV peptide tetramer to allow identification of CD8$^+$ T cells specific for the NLV peptide from the pp65 antigen of CMV. After washing in cold PBS, surface-labeled samples were analyzed on a BD LSR-2 flow cytometer. CMhi and EMhi subsets were identified as CD62L$^+$/CD161$^{hi}$ or CD62L$^-$/CD161$^{hi}$ events, respectively, in the CD4$^-$/CD16$^-$/TCRγδ$^-$/CD8$^+$/CD95$^+$ populations. Data is shown in FIG. 11a).

To demonstrate that rare tetramer-positive events seen in the CMhi and EMhi subsets ex vivo were viral antigen-specific CTL, we expanded antigen-specific CTL in vitro from isolated CMhi and EMhi subsets by culture with autologous activated peptide-pulsed monocyte-derived DC (MoDC). CMhi, CMlo, EMhi and EMlo were isolated as described in Example 6. MoDC were generated by culture of CD14$^+$ monocytes, isolated using CD14-specific paramagnetic beads, with GM-CSF (800 U/ml) and IL-4 (1000 U/ml) for 5 days. Mature MoDC were generated by culture to day 7 with additional GM-CSF (800 U/ml)/IL-4 (1000 U/ml) and IL-1β(2 ng/ml), IL-6 (1000 U/ml), PGE$_2$ (1000 ng/ml) and TNFα (10 ng/ml). Activated MoDC were pulsed in RPMI1640 (Gibco) for 2 hours at room temperature with 1 μg/ml HLA-A*0201-restricted NLVPMVATV, GLCTLVAML or GILGFVFTL peptides, derived from CMV, EBV or influenza, respectively. MoDC were washed 3 times in RPMI1640 and irradiated (3500 cGy) before use.

Figure 11B:
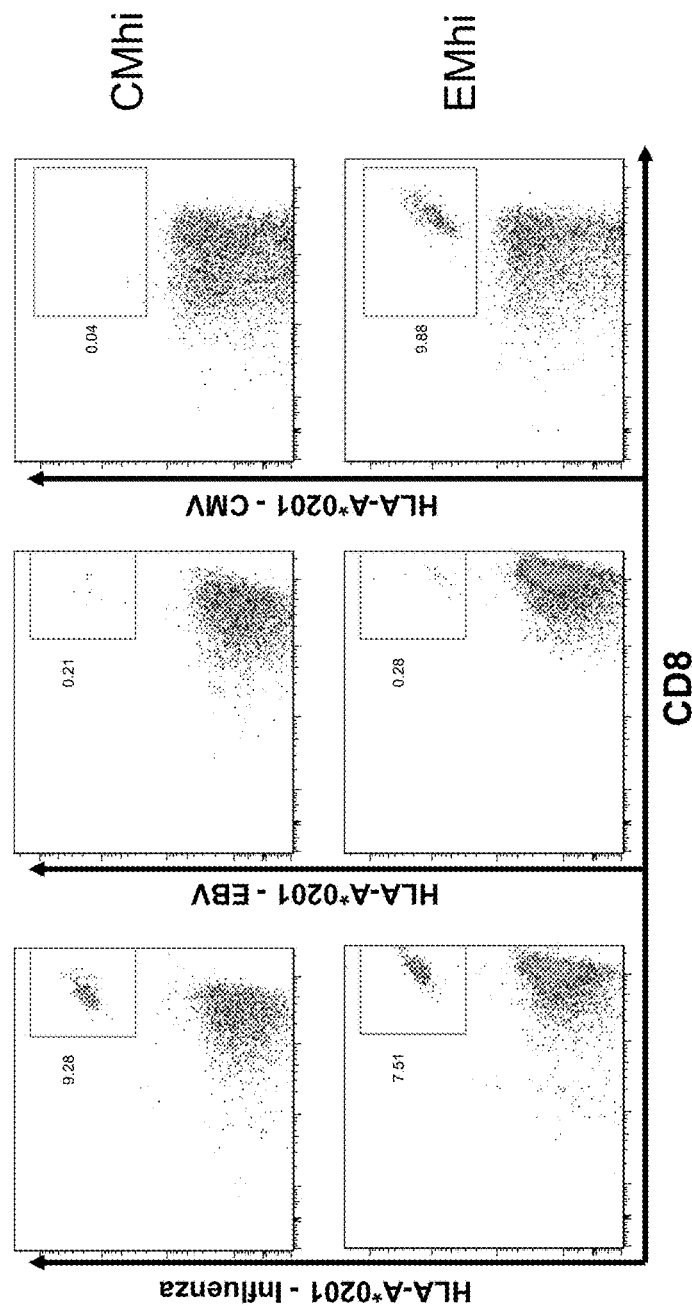
Figure 12:
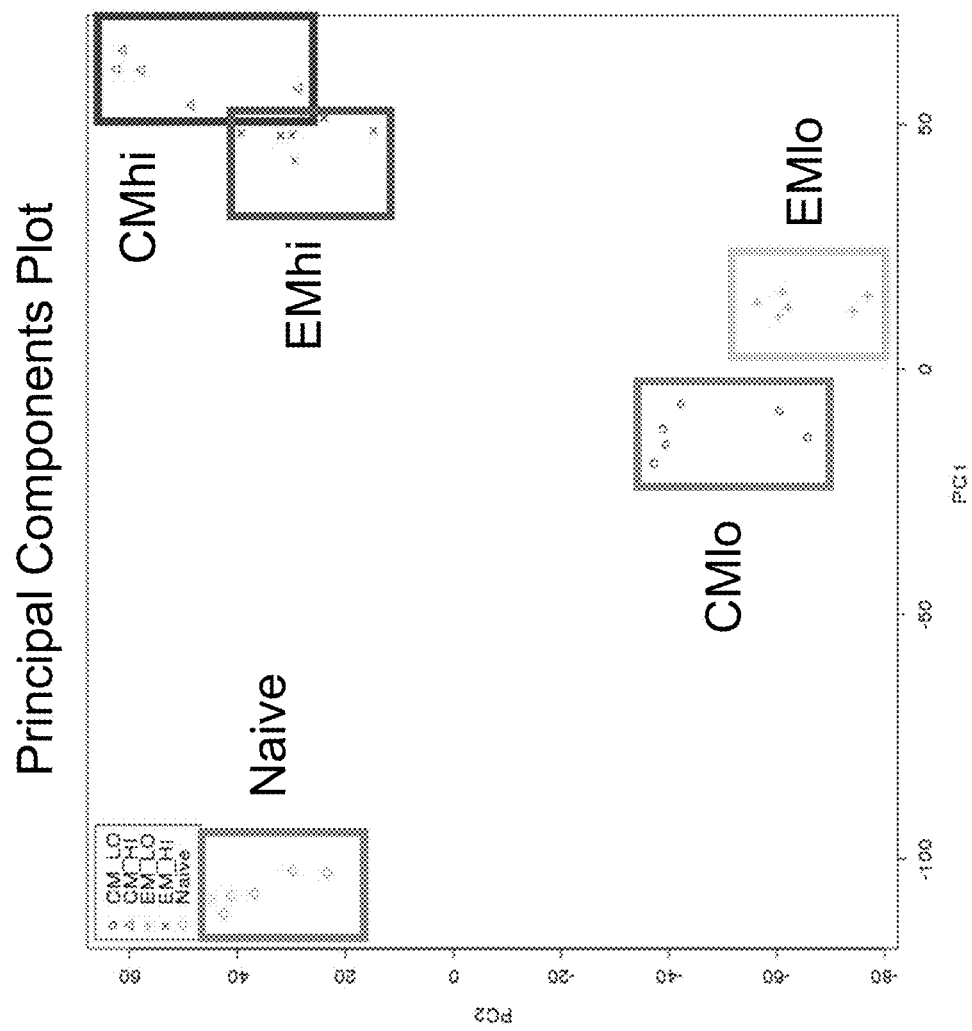
FIG. 12: CMhi and EMhi subsets have unique and distinct gene expression profiles as shown by the Principal Components Plot and as described in Example 12.

CMhi, CMlo, EMhi and EMlo subsets were plated in 96 well plates with irradiated, activated, peptide-pulsed MoDC at a T:DC ratio of 4:1 in 200 ml CTL medium supplemented with IL-2 (10 U/ml), IL7 (1 ng/ml) and IL-15 (100 pg/ml). Cytokine and half medium exchanges were performed on days 4 and 7 and analysis by CD8, DAPI and tetramer staining was performed on day 10. Data is shown in FIG. 11b).

This experiment demonstrates that rare virus-specific tetramer-positive CD8$^+$ T cells can be identified within rapidly effluxing CMhi and EMhi populations ex vivo and that rare viral antigen-specific CD8$^+$ T cells can be identified after in vitro stimulation of isolated effluxing CMhi and EMhi subsets. Despite the fact that effluxing CMhi and EMhi are refractory to stimulation with OKT3 (Example 7), proliferation can be rescued by culturing with cytokines. The use of activated MoDC and cytokine supplementation in Example 11 allows expansion of antigen-specific CTL from effluxing subsets in vitro.

Example 12

CMhi and EMhi Subsets Have Unique and Distinct Gene Expression Profiles

CMhi, CMlo, EMhi and EMlo were isolated as described in Example 6. PBMC were separated from fresh peripheral blood by density gradient centrifugation. CD8$^+$ T cells were positively selected using CD8-specific paramagnetic beads and resuspended at 1×10$^6$/ml in ice cold efflux buffer with 10 μg/ml Rh123. CD8$^+$ T cells were incubated for 30 minutes on ice before washing three times in ice cold efflux buffer and resuspending in pre-warmed efflux buffer, with or without vinblastine, for 30 minutes at 37° C. At 30 minutes, CD8$^+$ T cells were washed once in ice cold PBS/0.2% BSA (FACS buffer) and labeled with fluorochrome-conjugated antibodies to CD4, CD16, TCRγδ, Vα24, CD8α, CD95, CD62L and CD161. CMhi and EMhi subsets were identified as CD62L$^+$/Rh123$^{lo}$/CD161$^{hi}$ or CD62L$^-$/Rh123$^{lo}$/CD161$^{hi}$ events, respectively, in the CD4$^-$/CD16$^-$/TCRγδ$^-$/Vα24$^-$/CD8$^+$ population. CMlo and EMlo subsets were identified as CD62L$^+$/Rh123$^{hi}$/CD161$^{int/neg}$ or CD62L$^-$/Rh123$^{hi}$/CD161$^{int/neg}$ events, respectively, in the CD4$^-$/CD16$^-$/TCRγδ$^-$/Vα24$^-$/CD8$^+$/CD95$^+$ population. Subsets were isolated using a BD FacsARIA flow sorter.

cRNA was generated from isolated subsets and gene expression array studies were performed, using the Illumina HumanWG-6 expression beadchip array. The data are displayed on a Principal Components Plot to illustrate the gene expression relationships of CMhi and EMhi in relation to non-effluxing CD8$^+$ T cell subsets. The data show that rapidly effluxing (CMhi and EMhi) subsets have gene expression profiles that are distinct from those of naïve or non-effluxing memory (CMlo and EMlo) CD8$^+$ T cells. In addition, the separation of CMhi and EMhi clusters suggests that, despite their similar phenotype, CD62L$^+$ (CMhi) and CD62L$^-$ (CMlo) effluxing CD8$^+$ T cells have different gene expression profiles.

Example 13

Figures 13A, 13B:
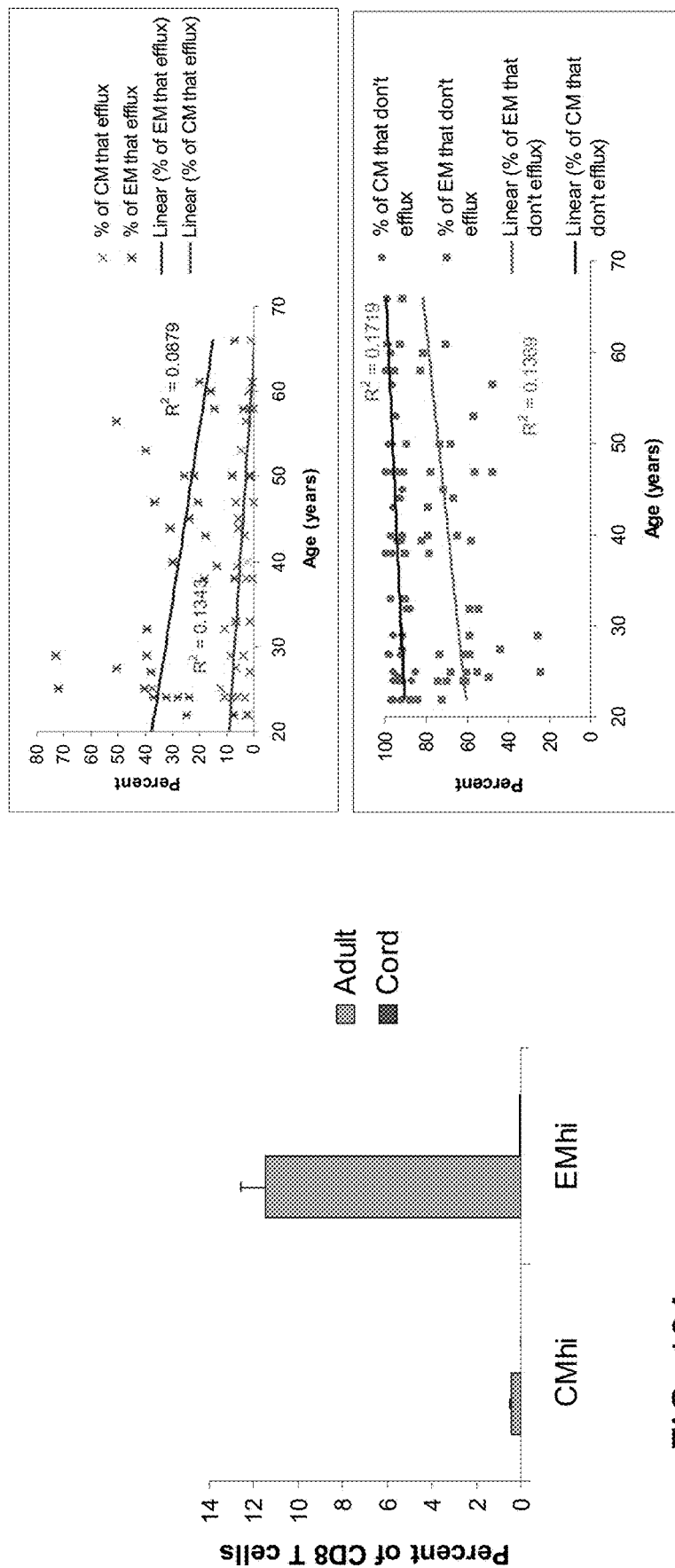
FIGS. 13A-13B: CMhi and EMhi are rare in cord blood, peak in early adult life and are found at decreasing frequency with advancing age, as described in Example 13.

CMhi and EMhi are Rare in Cord Blood, Peak in Early Adult Life and are Found at Decreasing Frequency with Advancing Age PBMC were separated from fresh peripheral blood or cord blood by density gradient centrifugation. CD8$^+$ T cells were positively selected using CD8 Microbeads (Miltenyi) and resuspended at 1×10$^6$/ml in ice cold efflux buffer with 10 μg/ml Rh123. CD8$^+$ T cells were incubated for 30 minutes on ice before washing three times in ice cold efflux buffer and resuspending in pre-warmed efflux buffer for 30 minutes at 37° C. Vinblastine was added to control samples to establish the presence of efflux). CD8$^+$ T cells were then washed once in ice cold PBS/0.2% BSA (FACS buffer) and labeled with fluorochrome-conjugated antibodies to CD4, CD16, TCRγδ, Vα24, CD8α, CD95, CD62L and CD161. CMhi and EMhi subsets were identified as CD62L$^+$/Rh123$^{lo}$/CD161$^{hi}$ or CD62L$^-$/Rh123$^{lo}$/CD161$^{hi}$ events, respectively, in the CD4$^-$/CD16$^-$/TCRγδ$^-$/Vα24$^-$/CD8$^+$ population. CMlo and EMlo subsets were identified as CD62L$^\pm$/Rh123hi/CD161$^{int/neg}$ or CD62L$^-$/Rh123$^{hi}$/CD161$^{int/neg}$ events, respectively, in the CD4$^-$/CD16$^-$/TCRγδ$^-$/Vα24$^-$/CD8$^+$/CD95$^+$ population. The gating strategy is shown in FIG. 6a). Samples were assayed using a BD FacsARIA flow cytometer. The frequency of CMhi and EMhi phenotype cells as a percentage of CD8$^+$ T cells is shown in cord blood compared to adult peripheral blood in FIG. 13a). The percentage of effluxing (top) and non-effluxing (bottom) cells in the parental CM and EM compartments are shown in FIG. 13b). Each point represents a single healthy donor.

The foregoing is illustrative of the present invention, and is not to be construed as limiting thereof. The invention is defined by the following claims, with equivalents of the claims to be included therein.

That which is claimed is:

1. A composition comprising an isolated population of long-lived human memory CD8+ CD161$^{hi}$ IL-18Rα$^{hi}$ T cells, wherein:
the long-lived memory CD8+ CD161$^{hi}$ IL-18Rα$^{hi}$ T cells make up at least 30% of the total CD8+ T cells in the composition; and
the long-lived memory CD8+ CD161$^{hi}$ IL-18Rα$^{hi}$ T cells comprise CD95$^{hi}$ memory cells, wherein the CD95$^{hi}$ memory cells are capable of proliferating in response to IL-7 or IL-15 and comprise a population of cells comprising an engineered immunoreceptor.

2. The composition of claim 1, wherein the population of long-lived memory CD8+ CD161$^{hi}$IL-18Rα$^{hi}$ T cells comprises high CD28 surface expression and high MDR-1 mRNA levels as compared to a CD8+ T cell population with low surface expression of IL-18Rα.

3. The composition of claim 1, wherein the long-lived memory CD8+ CD161$^{hi}$ IL-18Rα$^{hi}$ T cells are CD127$^{+}$, CD25$^{-}$, bcl-2$^{hi}$, perforin$^{neg/low}$, granzyme A$^{int}$, granzyme B$^{int/neg}$ and NKG2D$^{int}$.

4. The composition of claim 1, wherein the long-lived memory CD8+ CD161$^{hi}$ IL-18Rα$^{hi}$ T cell population has increased expression of CD43, CD44, CD46, CD148, and CD162 as compared to a CD8+ T cell population with low surface expression of IL-18Rα.

5. The composition of claim 1, wherein the long-lived memory CD8+ CD161$^{hi}$ IL-18Rα$^{hi}$ T cell population lacks expression of CD57, CD103, and CD69 as compared to a CD8+ T cell population with low surface expression of IL-18Rα.

6. The composition of claim 1, wherein the long-lived memory CD8+ CD161$^{hi}$ IL-18Rα$^{hi}$ T cell population increased expression of CD122 as compared to a CD8+ T cell population with low surface expression of IL-18Rα.

7. The composition of claim 1, wherein the CD95$^{hi}$ memory cells comprise CD62L$^{+}$, CD45RA$^{int/neg}$, CD45RO$^{int/hi}$ central memory cells.

8. The composition of claim 7, wherein the CD95$^{hi}$ memory cells further comprise CD62L$^{-}$, CD45RA$^{int/neg}$, CD45RO$^{int/hi}$ central memory cells.

9. The composition of claim 1, wherein the CD95$^{hi}$ memory cells comprise CD62L$^{-}$, CD45RA$^{int/neg}$, CD45RO$^{int/hi}$ central memory cells.

10. The composition of claim 1, wherein the engineered immunoreceptor is specific for a tumor-associated antigen.

11. The composition of claim 1, wherein the engineered immunoreceptor is an antigen-specific T cell receptor.

12. The composition of claim 1, wherein the long-lived memory CD8+ CD161$^{hi}$ IL-18Rα$^{hi}$ T cells are at least 40% of the total CD8+ T cells in the composition.

13. The composition of claim 1, wherein the long-lived memory CD8+ CD161$^{hi}$ IL-18Rα$^{hi}$ T cells are at least 50% of the total CD8+ T cells in the composition.

14. The composition of claim 1, wherein the long-lived memory CD$^{8}$+ CD161$^{hi}$ IL-18Rα$^{hi}$ T cells are at least 80% of the total CD8+ T cells in the composition.

15. The composition of claim 1, wherein the long-lived memory CD8+ CD161$^{hi}$IL-18Rα$^{hi}$ T cells have enhanced proliferation in response to a cytokine selected from the group consisting of IL-12, Il-18, IL-23, or combinations thereof, as compared to a CD8+T cell population with low surface expression of IL-18Rα.

* * * * *